(12) United States Patent
Burrows-Ownbey et al.

(10) Patent No.: US 10,702,396 B2
(45) Date of Patent: Jul. 7, 2020

(54) SURGICAL OPERATING INSTRUMENT FOR EXPANDABLE AND ADJUSTABLE LORDOSIS INTERBODY FUSION SYSTEMS

(71) Applicant: SpineEx, Inc., Fremont, CA (US)

(72) Inventors: Robyn Burrows-Ownbey, Kansas City, MO (US); Andrew Rogers, Deephaven, MN (US)

(73) Assignee: SpineEX, Inc., Fremont, CA (US)

( * ) Notice: Subject to any disclaimer, the term of this patent is extended or adjusted under 35 U.S.C. 154(b) by 262 days.

(21) Appl. No.: 15/661,435

(22) Filed: Jul. 27, 2017

(65) Prior Publication Data

US 2018/0125677 A1     May 10, 2018

Related U.S. Application Data

(63) Continuation-in-part of application No. 14/473,200, filed on Aug. 29, 2014, now Pat. No. 9,889,019.

(Continued)

(51) Int. Cl.
*A61F 2/46*     (2006.01)
*A61F 2/44*     (2006.01)
(Continued)

(52) U.S. Cl.
CPC ............ *A61F 2/4611* (2013.01); *A61F 2/447* (2013.01); *A61F 2/4465* (2013.01); *A61F 2/4601* (2013.01); *A61F 2/4614* (2013.01); *A61B 17/025* (2013.01); *A61B 2017/00367* (2013.01); *A61B 2017/00407* (2013.01); *A61B 2017/00424* (2013.01); *A61B 2017/00477* (2013.01); *A61B 2017/0256* (2013.01); *A61F 2002/30579* (2013.01); *A61F 2002/4475* (2013.01); *A61F 2002/4624* (2013.01);
(Continued)

(58) Field of Classification Search
CPC .................. A61F 2/4611; A61F 2/4612; A61F 2002/4625; A61F 2002/4627; A61F 2002/4628; A61B 17/8894; A61B 17/8875; A61B 17/885; B25B 17/00
USPC .......................... 81/57.22, 57.3, 57.32, 57.34
See application file for complete search history.

(56) References Cited

U.S. PATENT DOCUMENTS 4,453,434 A * 6/1984 Lissy .................... B25B 13/481
                                                                   74/553
4,515,043 A * 5/1985 Gray ..................... B23P 19/069
                                                                  74/665 GB (Continued)

*Primary Examiner* — Amy R Sipp
(74) *Attorney, Agent, or Firm* — SpineEX, Inc.

(57) ABSTRACT

A surgical operating instrument includes a handle, a first driving shaft operably connected with the handle, a second driving shaft, and a gear assembly. The gear assembly includes a first gear member received on the first driving shaft, a second gear member slidably received on the second driving shaft, and a lever member. The lever member is operable to place the second gear member into engagement with the first gear member thereby coupling the second driving shaft with the first driving shaft to provide a first operating mode wherein the handle operates to rotate both the first and second driving shafts, and place the second gear member out of engagement with the first gear member thereby decoupling the second driving shaft from the first driving shaft to provide a second operating mode wherein the handle operates to rotate solely the first driving shaft.

21 Claims, 31 Drawing Sheets

Related U.S. Application Data

(60) Provisional application No. 61/871,780, filed on Aug. 29, 2013.

(51) Int. Cl.
    *A61F 2/30*        (2006.01)
    *A61B 17/00*      (2006.01)
    *A61B 17/02*      (2006.01)

(52) U.S. Cl.
    CPC ................ *A61F 2002/4627* (2013.01); *A61F 2002/4628* (2013.01); *A61F 2002/4629* (2013.01)

(56) References Cited

U.S. PATENT DOCUMENTS

| | | | | |
|---|---|---|---|---|
| 5,572,905 A | * | 11/1996 | Cook, Jr. | B23P 19/069 464/37 |
| 2007/0123905 A1 | * | 5/2007 | Schneid | A61F 2/4425 606/99 |
| 2008/0021558 A1 | * | 1/2008 | Thramann | A61F 2/447 623/17.16 |
| 2010/0160984 A1 | * | 6/2010 | Berry | A61F 2/447 606/86 A |
| 2012/0158071 A1 | * | 6/2012 | Jimenez | A61F 2/4611 606/86 A |
| 2014/0013903 A1 | * | 1/2014 | Singh Sidhu | B25B 13/463 81/58 |
| 2015/0351925 A1 | * | 12/2015 | Emerick | A61F 2/447 623/17.16 |
| 2016/0089247 A1 | * | 3/2016 | Nichols | A61F 2/30767 623/17.16 |

\* cited by examiner

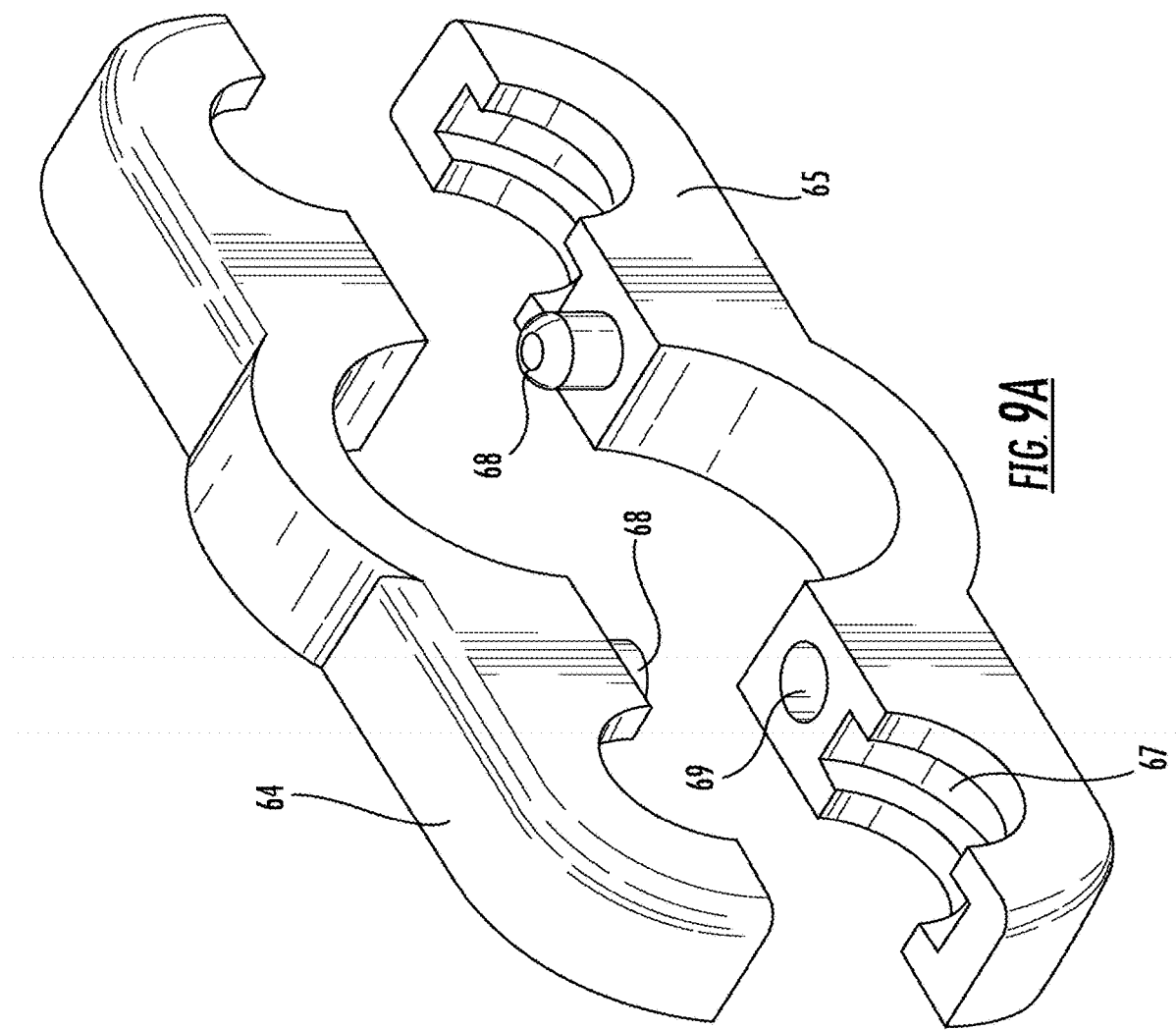

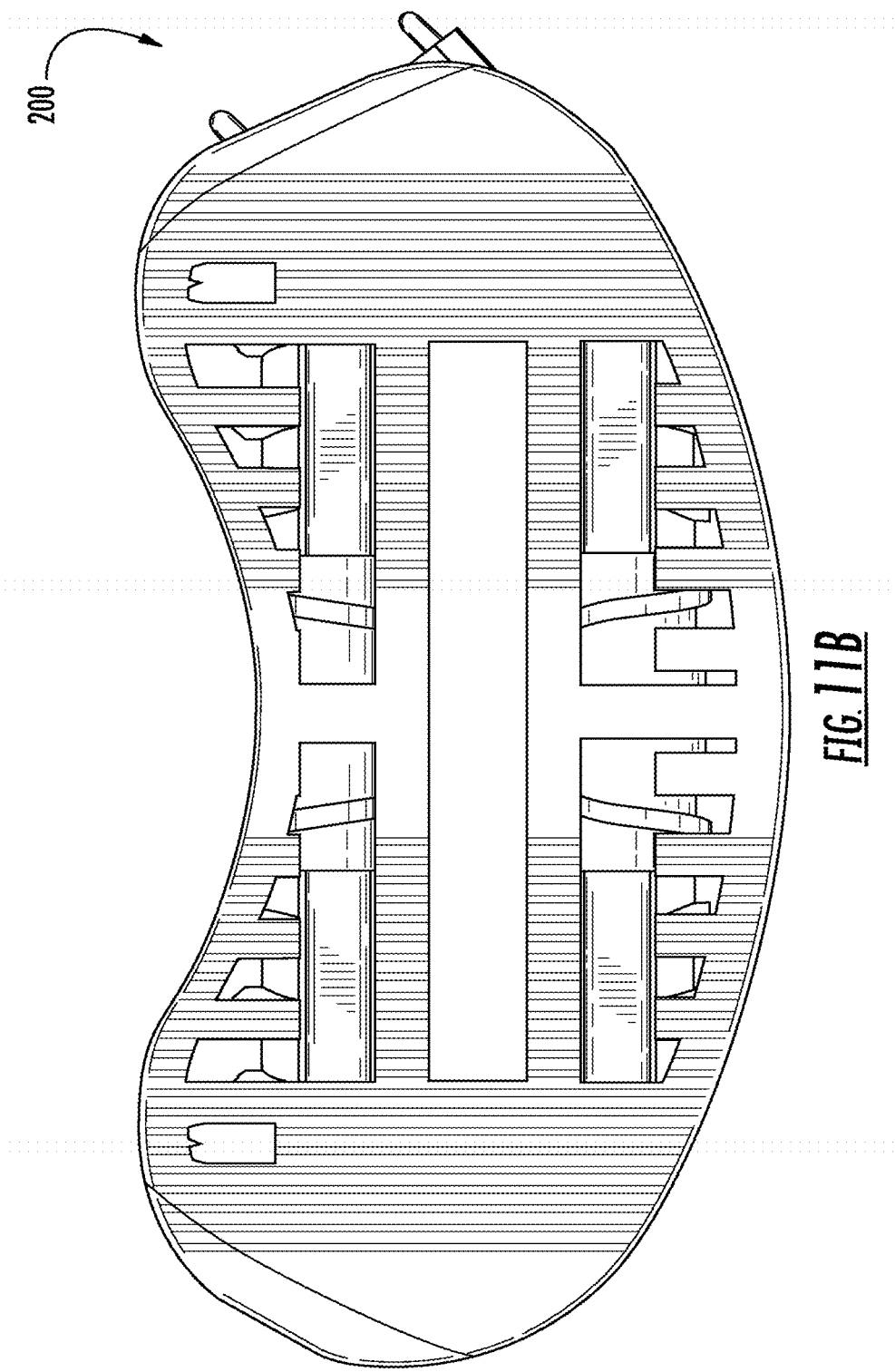

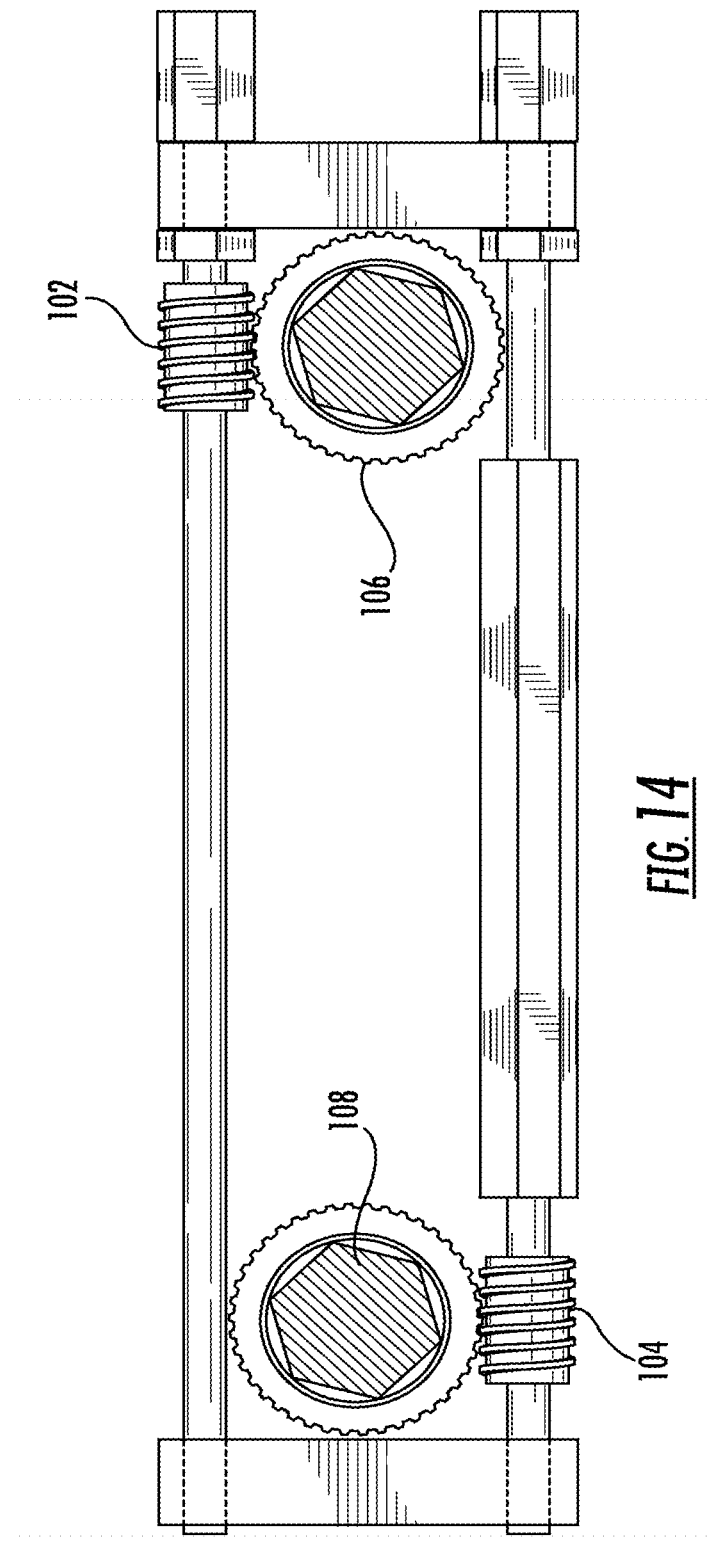

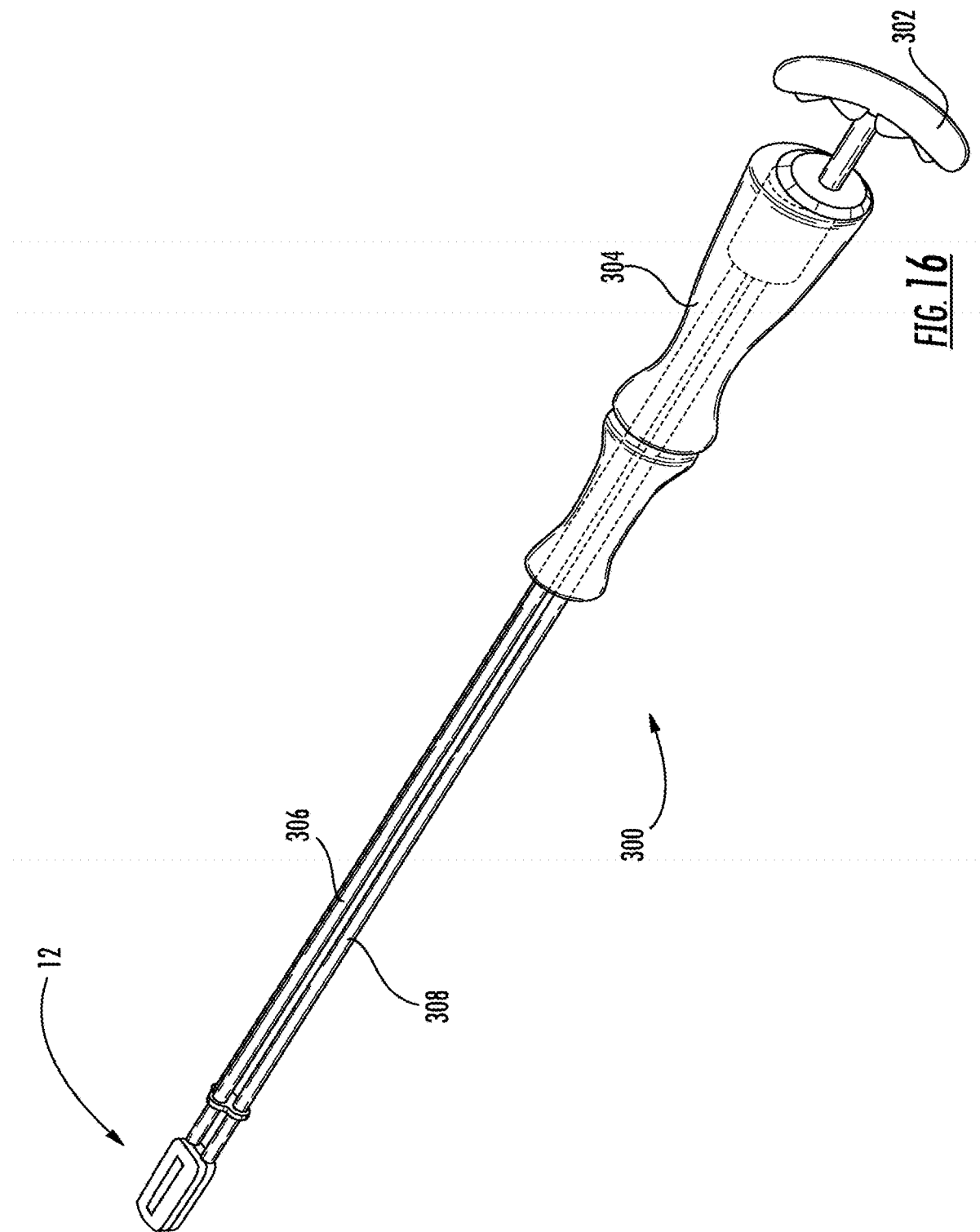

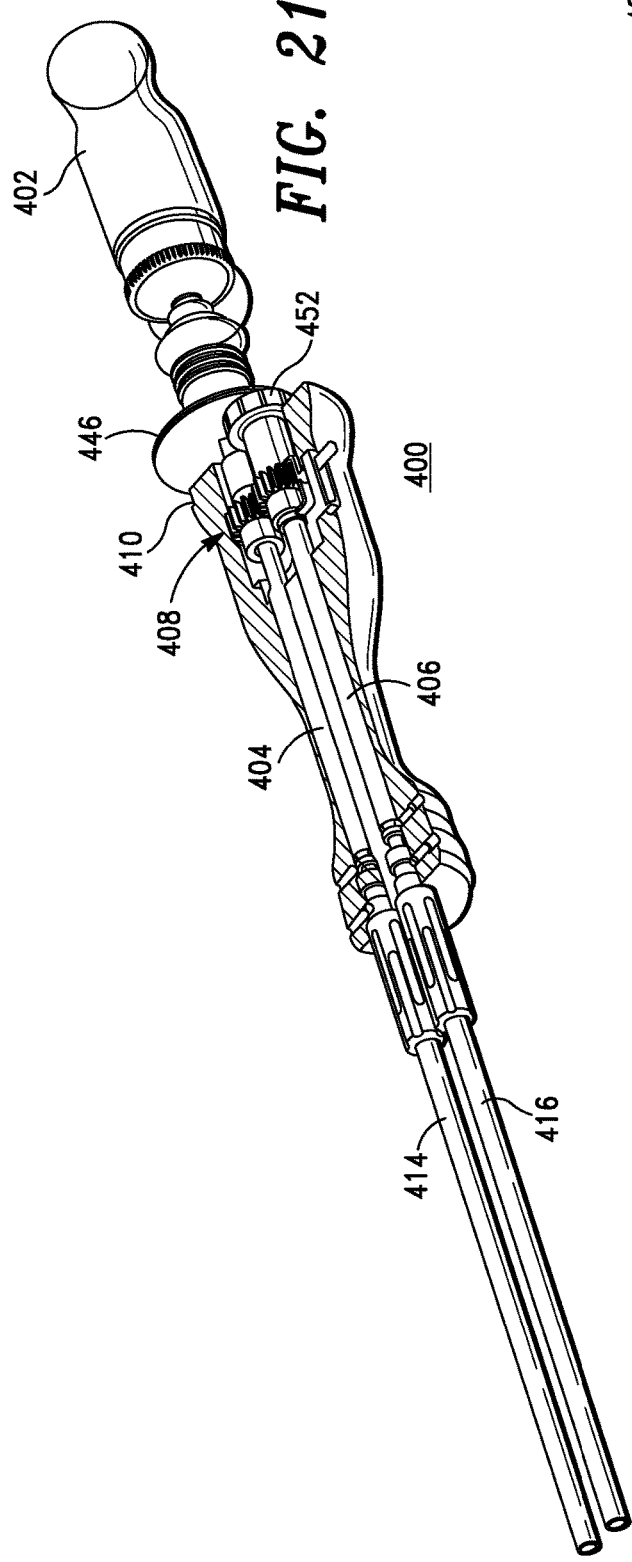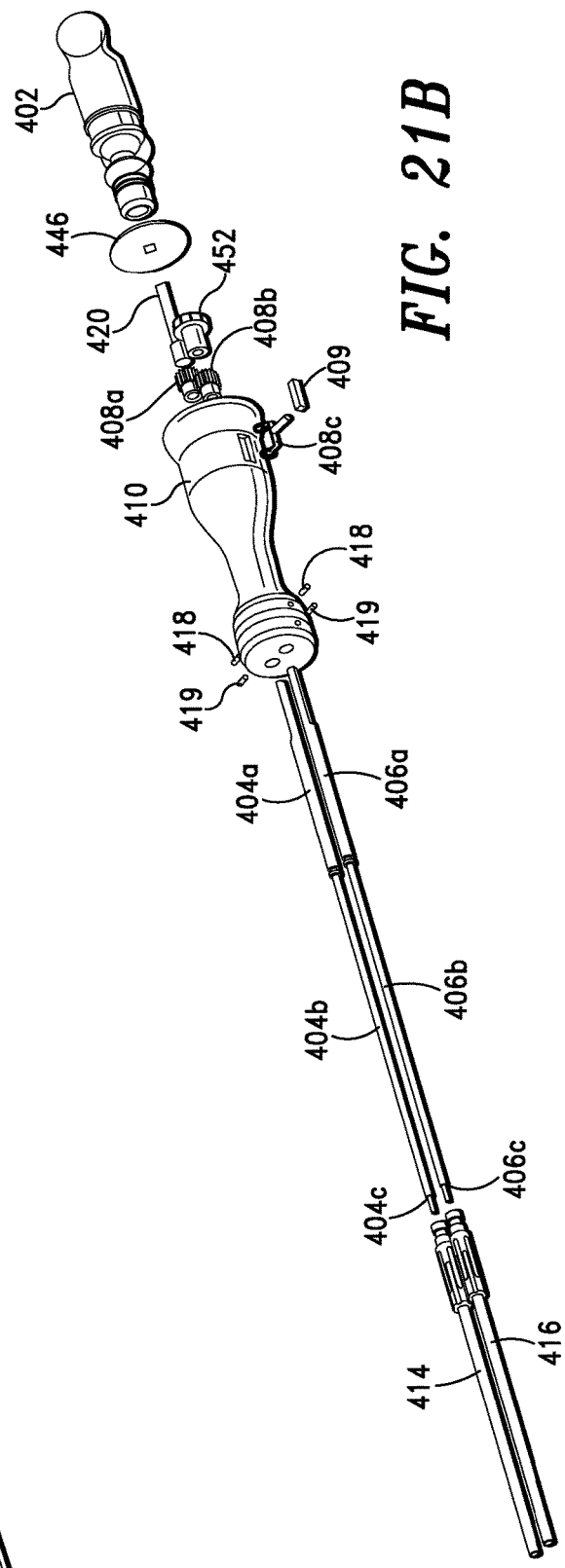

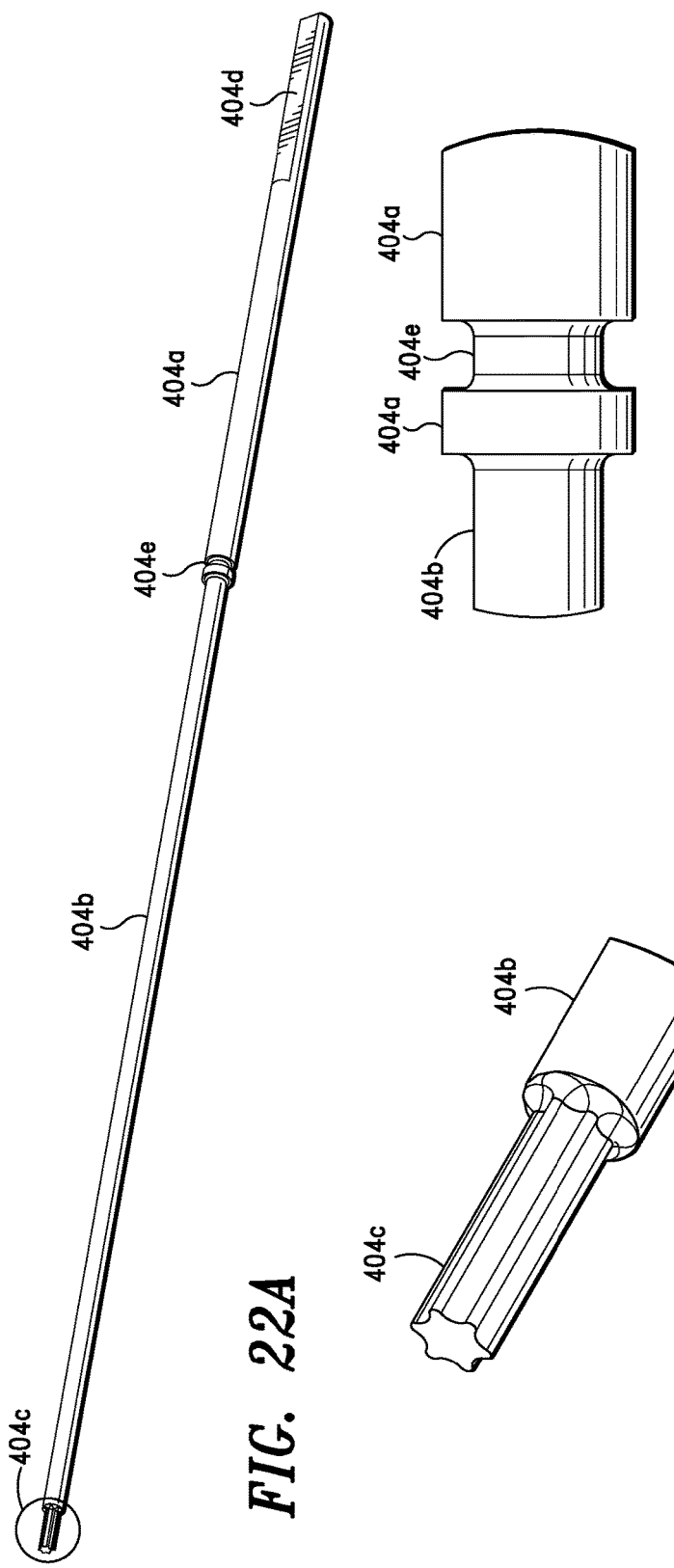
FIG. 22A
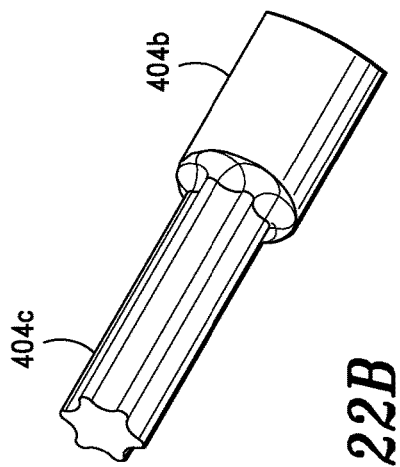
FIG. 22B
FIG. 22C
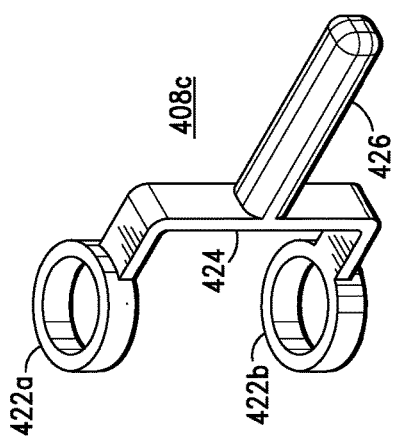
FIG. 23

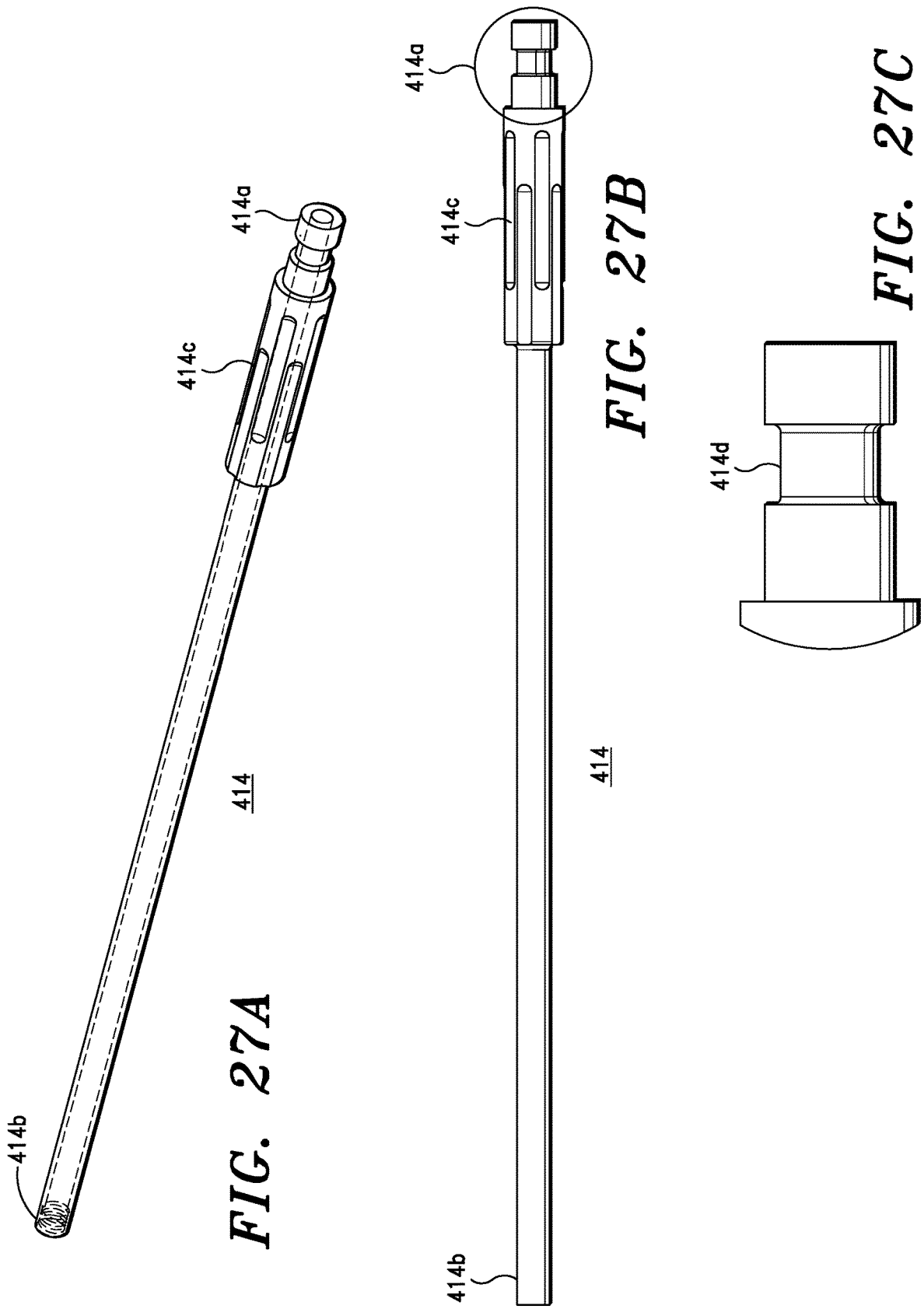

SURGICAL OPERATING INSTRUMENT FOR EXPANDABLE AND ADJUSTABLE LORDOSIS INTERBODY FUSION SYSTEMS

TECHNICAL FIELD

The invention relates to surgical procedures and apparatus for treating lumbar back pain.

BACKGROUND OF THE INVENTION

Lumbar spinal fusion is a surgical procedure to correct problems relating to the human spine. It generally involves removing damaged disc and bone from between two vertebrae and inserting bone graft material that promotes bone growth. As the bone grows, the two vertebrae join, or fuse, together. Fusing the bones together can help make that particular area of the back more stable and help reduce problems related to nerve irritation at the site of the fusion. Fusions can be done at one or more segments of the spine.

Interbody fusion is a common procedure to remove the nucleus pulposus and or the annulus fibrosus that compose the intervertebral disc at the point of the back problem and replace it with a cage configured in shape and dimension to restore the distance between adjacent vertebrae to that of a proper condition. Surgical approaches to implement interbody fusion vary, and access to the patient's vertebral column can be made through the abdomen or back. One other surgical method for accomplishing lumbar spinal fusion in a less invasive way involves accessing the vertebral column through a small incision on the side of the body. This procedure is known as lateral lumbar interbody fusion.

Once the intervertebral disc is removed from the body during the lateral lumbar interbody fusion, the surgeon typically forces different trial implants between the vertebral endplates of the specific region to determine the appropriate size of the implant for maintaining a distance between the adjacent vertebrae. Another consideration is to maintain the natural angle between lumbar vertebral bodies to accommodate the lordosis, or natural curvature, of the spine. Therefore, during selection of a cage for implantation, both intervertebral disc height and lordosis must be considered. Prior art fusion cages are often pre-configured to have top and bottom surfaces angles to one another to accommodate the natural curvature of the spine. It is unlikely that these values can be determined precisely prior to the operation, which is a drawback in present procedures. Prepared bone graft is generally packed into the cage implant once it is properly sized and before it is inserted in between the vertebral bodies.

Present lateral interbody fusion cage devices are generally limited to providing height expansion functions, but not a lordotic adjustment capability. In implementing a trial-and-error approach to sizing and fitting the interbody fusion cage into the target region for the particular geometric configuration for that patient, the patient is subjected to significant invasive activity. The bone graft material is generally added and packed in to the fusion device after the desired height expansion has been reached and final adjustments made.

SUMMARY OF THE INVENTION

An embodiment of the device comprises an expandable housing comprised of opposing shell members. Movable tapered screw-like elements having an external helical thread are disposed in the housing and operably engage against the top and bottom shell members, urging them apart to cause expansion in the height of the housing. This function permits adjustment of the distance (height) between adjacent vertebrae when in place. The tapered members are disposed in a dual arrangement such that independent engagement of the tapered members along lateral portions of the top and bottom shells cause an angular tilt to the exterior surface of the housing when the wedge members are moved to different degrees. This function permits adjustment in the angular relationship between adjacent vertebrae and assists the lordotic adjustment of the patient's spine. When the functions of the device are used in combination by the surgeon, the device provides an effective tool for in situ adjustment when performing lateral lumbar interbody fusion.

An embodiment of the device further comprises a track configuration within the housing for guiding the tapered external helical threaded members in their engagement with the top and bottom shell members. The track comprises raised elements on each of the interior surfaces of the top and bottom shell members that permit an interlocking engagement for lateral stability of the housing when in a contracted position. As the housing expands, the track area provides space for storage of bone graft material. One embodiment may provide for an elastic membrane to be positioned around the housing to prevent bone graft material from seeping out of the cage and to provide a compressive force around the cage to provide structural stability to the housing An embodiment of the device further comprises drive shafts for operating the tapered external helical threaded members. The drive shafts permit the surgeon, through the use of a supplemental tool, to manipulate the shafts which operatively move the tapered external helical threaded members in controlling the expansion of the housing and angular adjustment of the top and bottom shell members for in situ fitting of the interbody fusion device. A locking mechanism is provided for preventing rotation of the shafts when the tool is not engaged and after manipulation by the tool is completed. The tool also facilitates insertion of bone graft material into the fusion body during in situ adjustment.

An embodiment of the present invention provides a surgeon with the ability to both expand the fusion cage and adjust the lordotic angle of the fusion cage in situ during operation on a patient and to introduce bone graft material at the operation site while the device is in place. This embodiment of the present invention therefore provides a fusion cage having geometric variability to accommodate the spinal condition unique to each patient.

Embodiments of the present invention therefore provide an interbody cage device for use in lateral lumbar interbody fusion procedures that combines the functions of height expansion for adjusting the distance between adjacent vertebrae with lordotic adjustment to control the angular relationship between the vertebrae. Embodiments of the inventive interbody cage device further provide a storage capacity for containing bone graft material in the interbody cage device as disc height and lordotic adjustment takes place in situ.

The present invention also provides a device that may be used in environments other than in interbody fusion applications. It may generally be used to impart a separating effect between adjacent elements and to impart a variable angular relationship between the elements to which it is applied.

An embodiment of an operating instrument comprises a handle, a first driving shaft, a second driving shaft, and a gear assembly. The first driving shaft is operably connected with the handle. The gear assembly comprises a first gear member received on the first driving shaft, a second gear member slidably received on the second driving shaft, and a lever member. The lever member is operable to place the second gear member into engagement with the first gear member thereby coupling the second driving shaft with the first driving shaft to provide a first operating mode wherein the handle operates to rotate both the first and second driving shafts, or place the second gear member out of engagement with the first gear member thereby decoupling the second driving shaft from the first driving shaft to provide a second operating mode wherein the handle operates to rotate solely the first driving shaft.

An embodiment of an operating instrument comprises a handle, a housing, a first and a second driving shaft, a first and a second tubular shaft, and a gear assembly. The first driving shaft is operably connected with the handle, rotatably secured to the housing, and comprise a first portion received in the housing and a second portion extending out of the housing. The second driving shaft is rotatably secured to the housing and comprises a first portion received in the housing and a second portion extending out of the housing. The first tubular shaft surrounds the second portion of the first driving shaft and is rotatably secured to the housing. The second tubular shaft surrounds the second portion of the second driving shaft and is rotatably secured to the housing. The gear assembly is received in the housing operable to couple the second driving shaft with the first driving shaft to provide a first operating mode wherein the handle operates to rotate both the first and second driving shafts, or decouple the second driving shaft from the first driving shaft to provide a second operating mode wherein the handle operates to rotate solely the first driving shaft.

These and other features of the present invention are described in greater detail below in the section titled DETAILED DESCRIPTION OF THE INVENTION.

BRIEF DESCRIPTION OF THE DRAWINGS FIGURES

An embodiment of the present invention is described herein with reference to the following drawing figures, with greater emphasis being placed on clarity rather than scale:

FIG. 9A is a perspective expanded view of thrust bearing for the drive shaft.

FIG. 11B is a top plan view of yet another embodiment of the device.

FIG. 14 is a view taken along lines 14-14 in FIG. 11A.

Figure 15A:
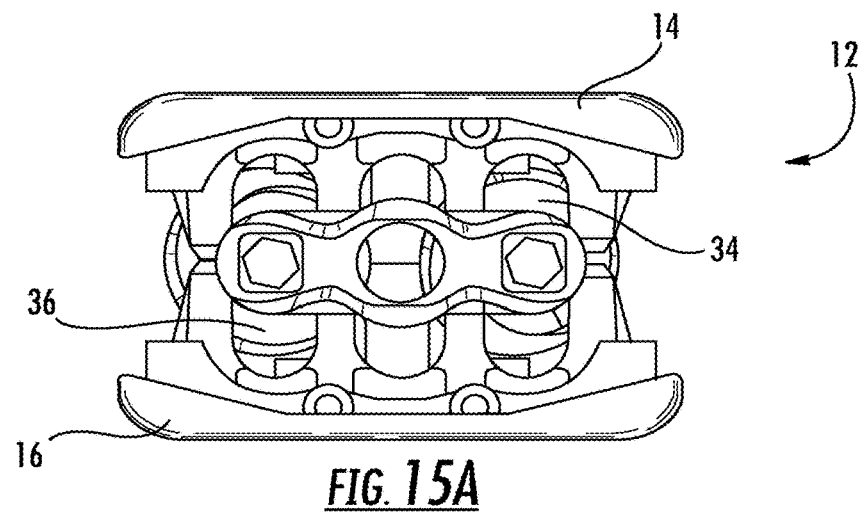
Figure 15B:
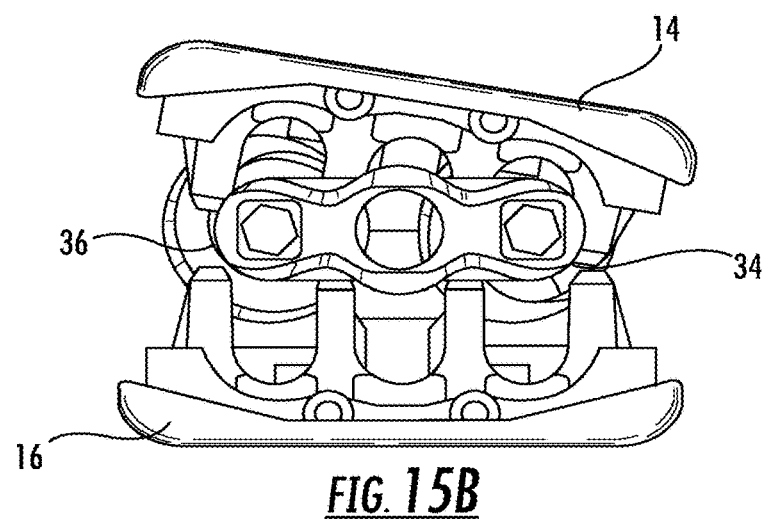
Figure 15C:
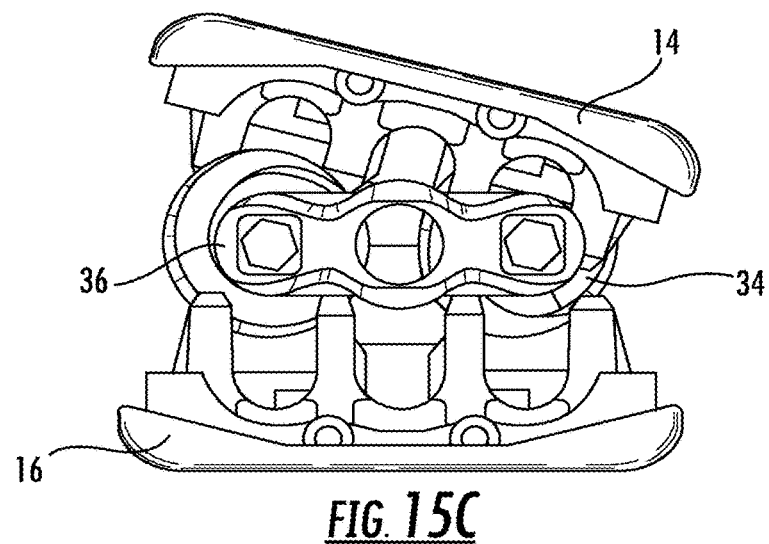

FIGS. 15A-C are a series of views in side elevation taken from the end of the device as it undergoes expansion showing the lordotic effect.

FIG. 16 is a perspective view of the operating tool.

Figure 17:
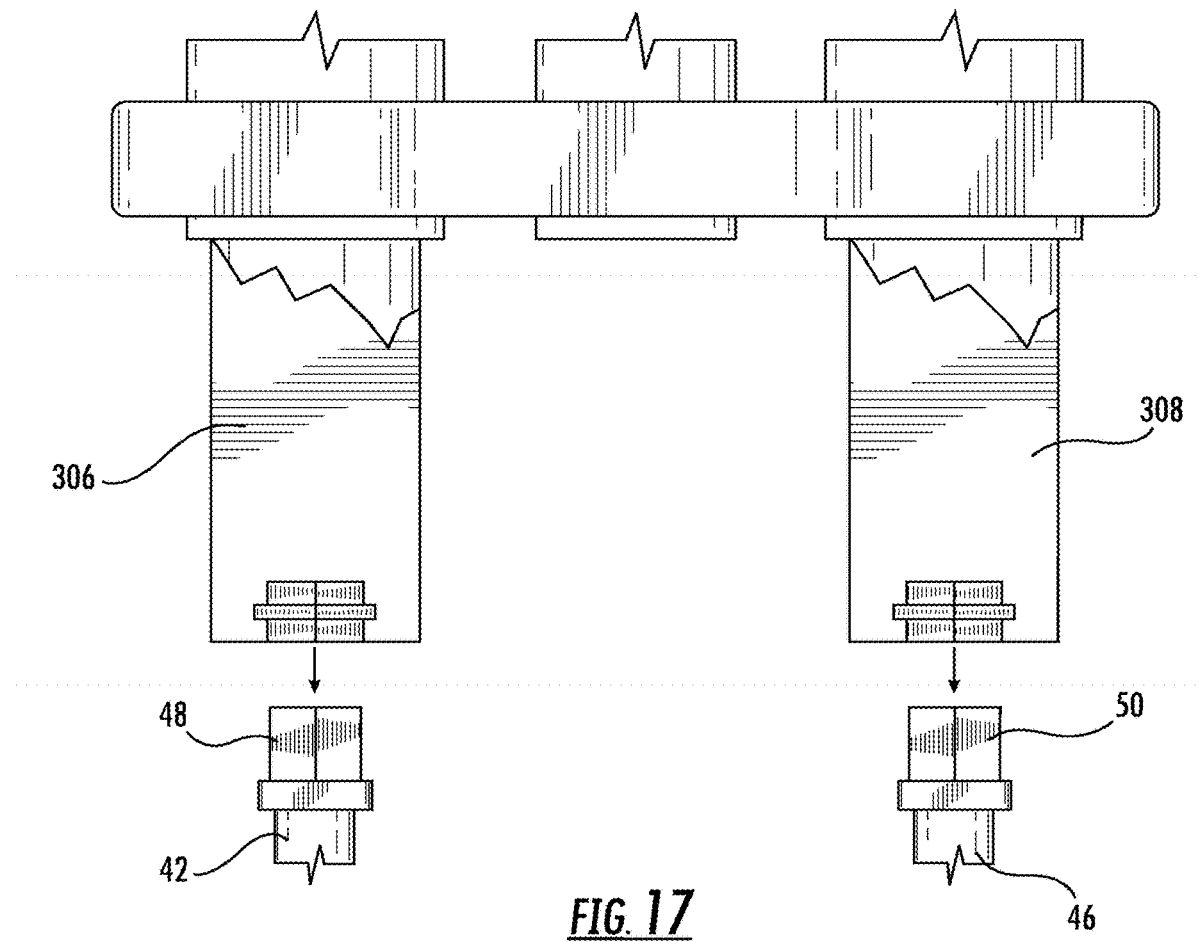

FIG. 17 is a view showing a manner of attachment of the operating tool to the drive shafts of the device.

Figure 18:
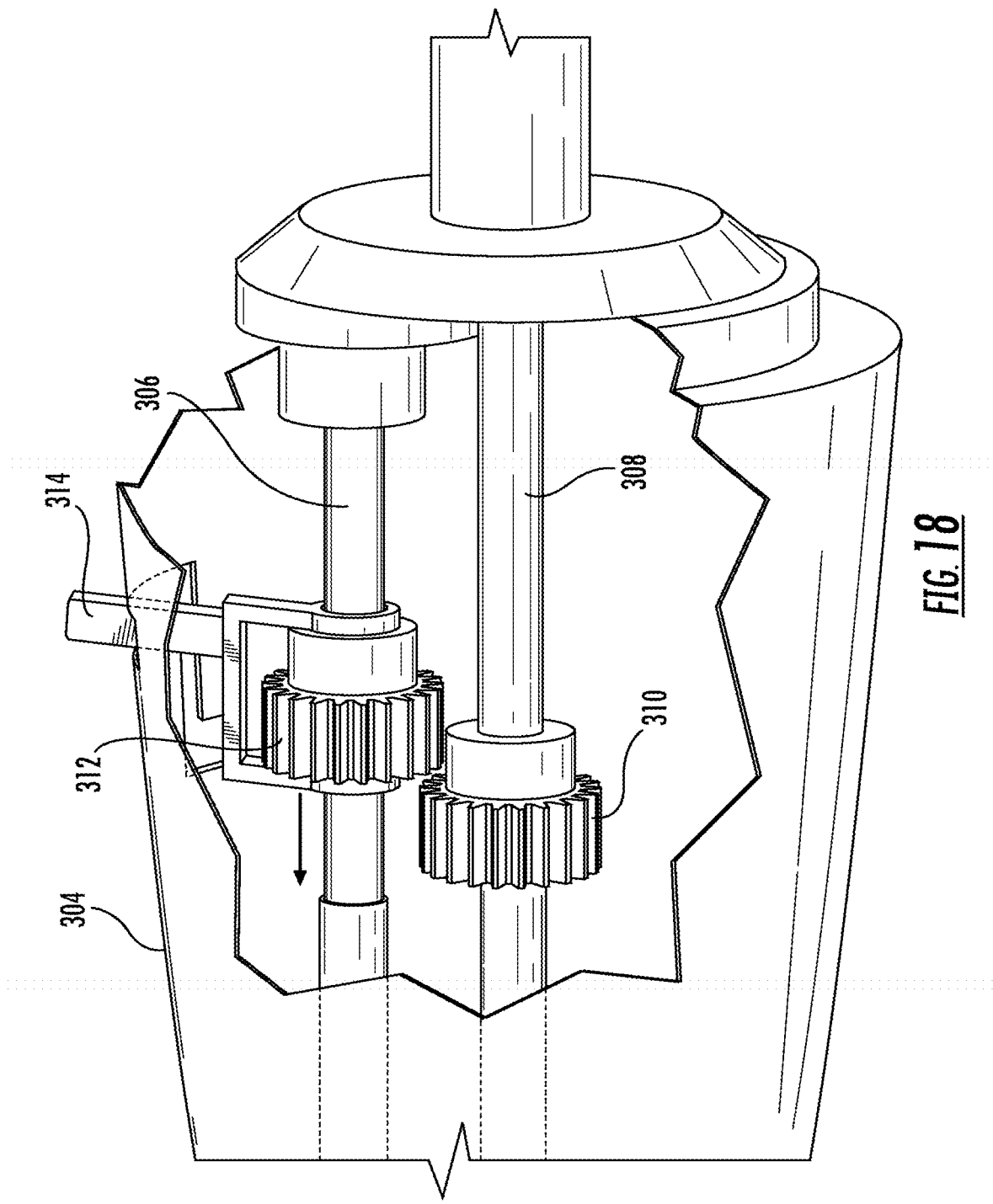

FIG. 18 is a breakaway perspective view of the handle of the operating tool.

Figure 19:
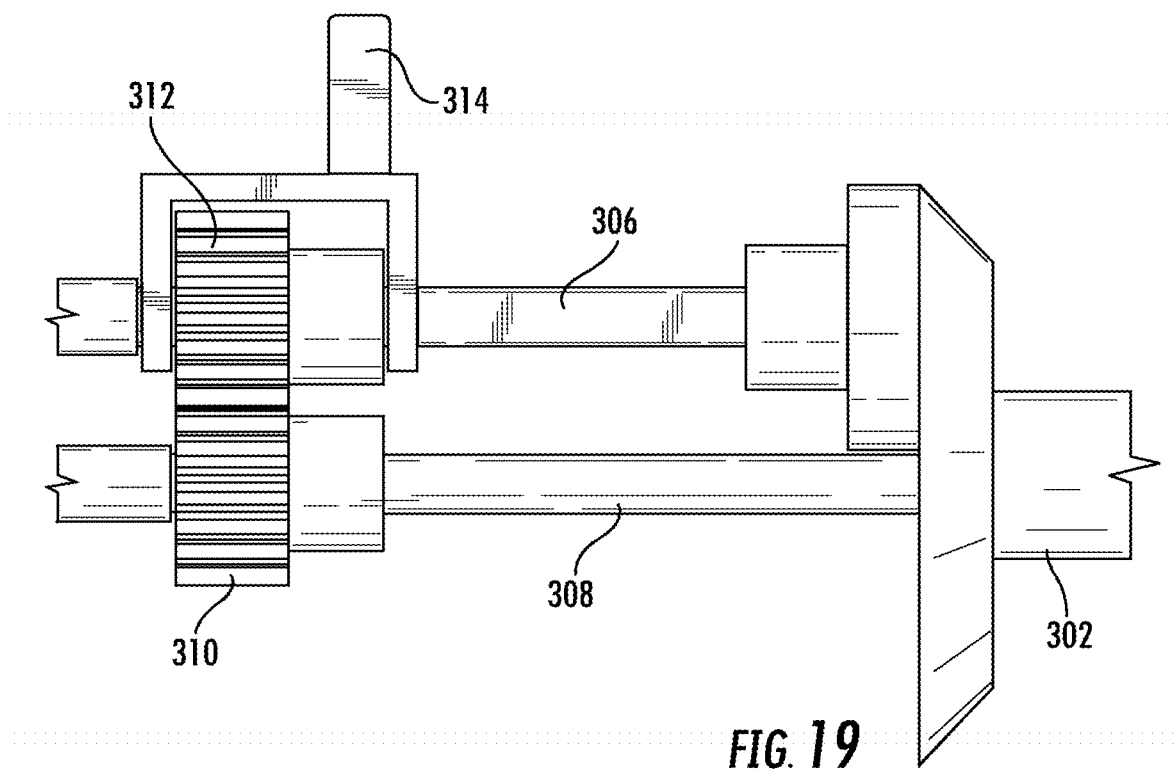

FIG. 19 is a perspective view of gears in the handle engaged for operation of both drive shafts.

Figure 20:
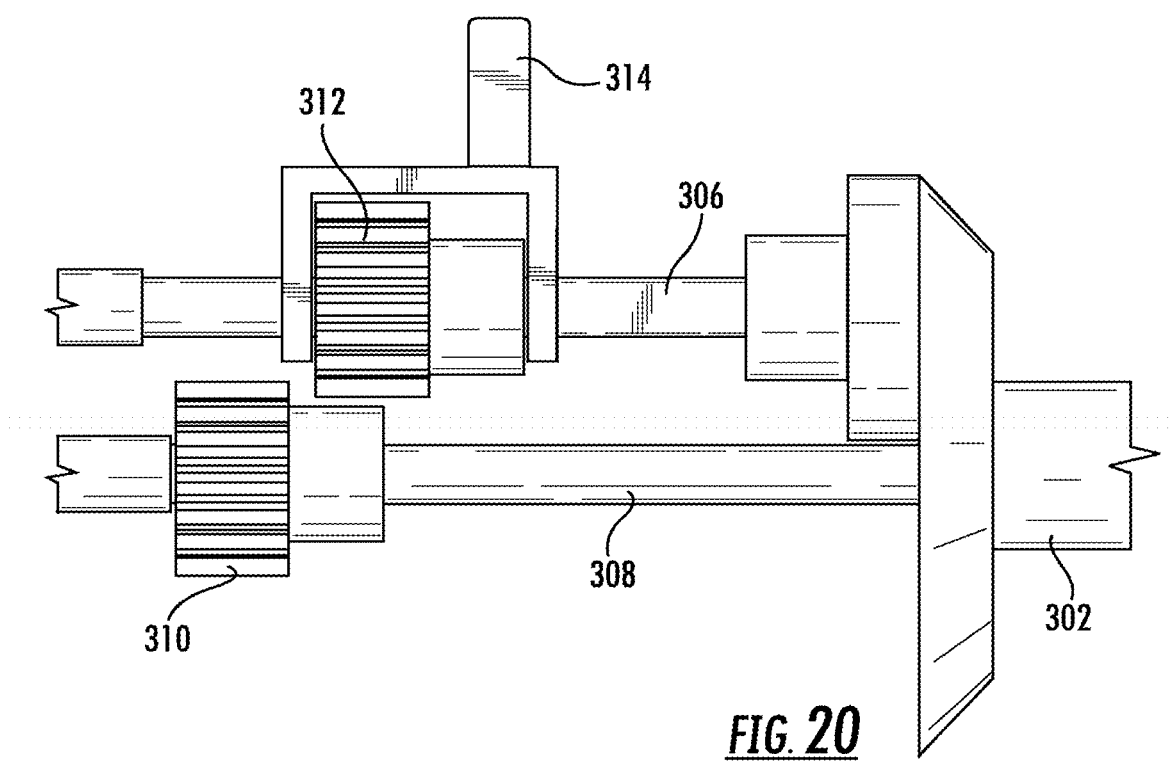

FIG. 20 is a perspective view of gears in the handle disengaged for operation of a single drive shaft.

FIG. 21A is a cutaway perspective view of an exemplary operating instrument according to embodiments of the disclosure.

FIG. 21B is an exploded perspective view of the operating instrument shown in FIG. 21A.

FIG. 22A is a perspective view of a driving shaft according to embodiments of the disclosure FIG. 22B is an enlarged perspective view of the tip portion of the driving shaft shown in FIG. 22A.

FIG. 22C is an enlarge plan view of a portion of the driving shaft shown in FIG. 22A.

FIG. 23 is a perspective view of an exemplary lever member according to embodiments of the disclosure.

Figure 24:
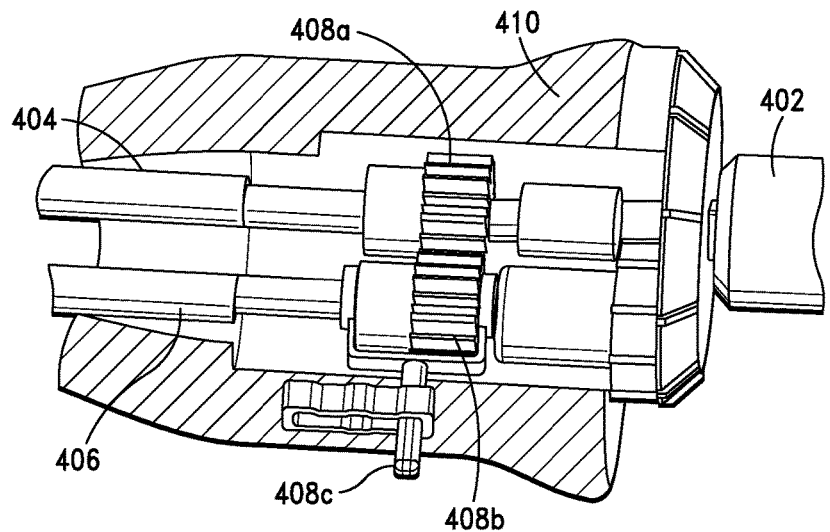

FIG. 24 is a perspective view of a portion of the operating instrument shown in FIG. 21A, illustrating a lever member in an expanded position with greater clarity.

Figure 25:
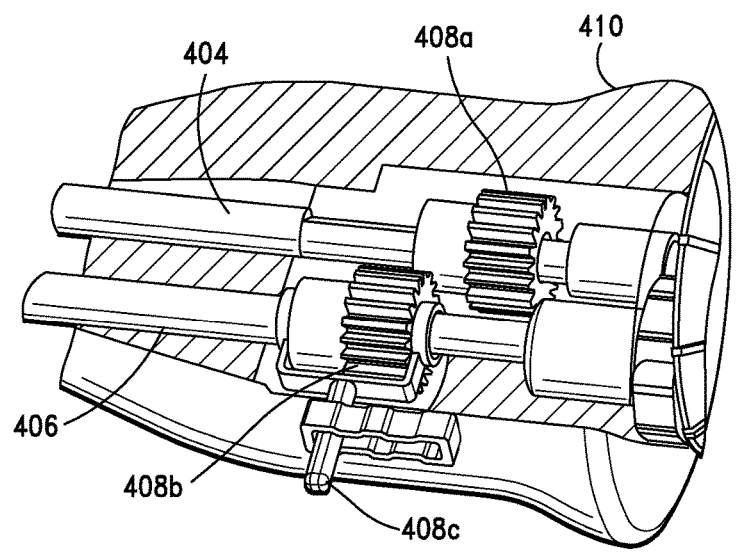

FIG. 25 is a perspective view of a portion of the operating instrument shown in FIG. 21A, illustrating a lever member in a lordosis position with greater clarity.

Figure 26:
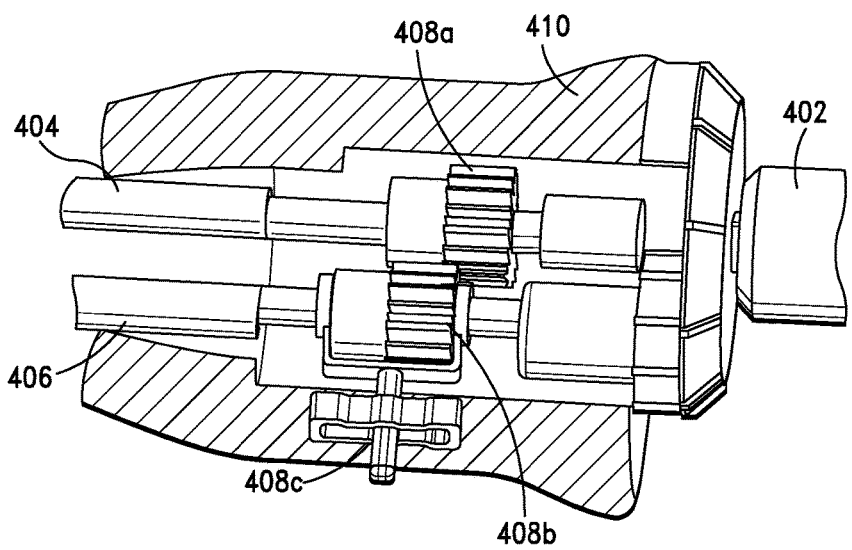

FIG. 26 is a perspective view of a portion of the operating instrument shown in FIG. 21A, illustrating a lever member in a locked position with greater clarity.

FIG. 27A is a perspective view of an exemplary outer connection shaft according to embodiments of the disclosure.

FIG. 27B is a plan view of the outer connection shaft shown in FIG. 27A.

FIG. 27C is a plan view of an end portion of the outer connection shaft shown in FIG. 27B.

Figure 28A:
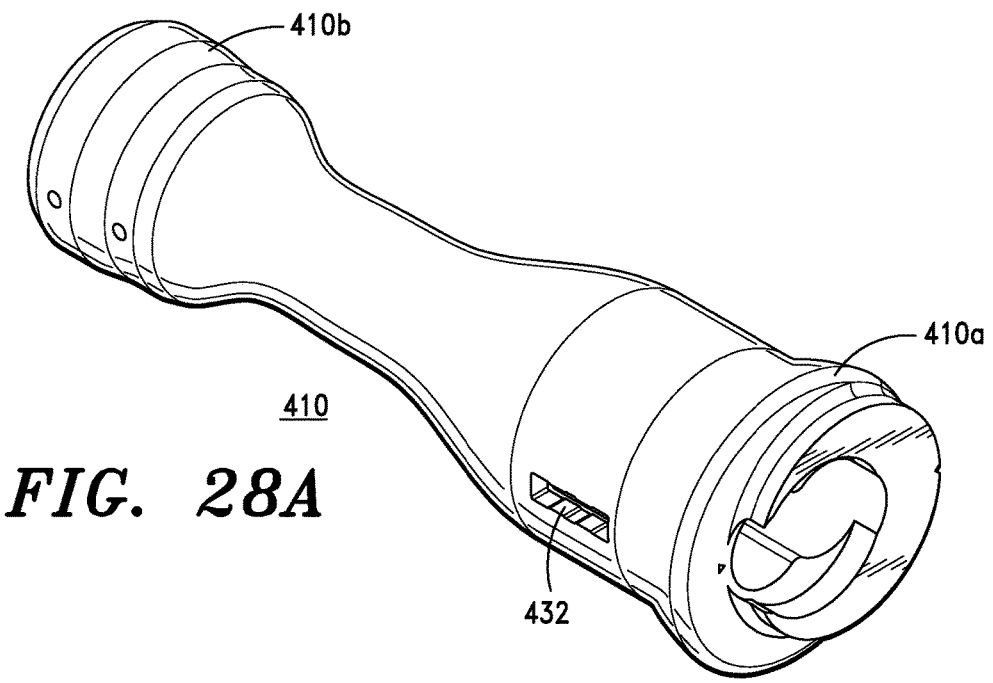

FIG. 28A is a perspective view of an exemplary handle according to embodiments of the disclosure.

Figure 28B:
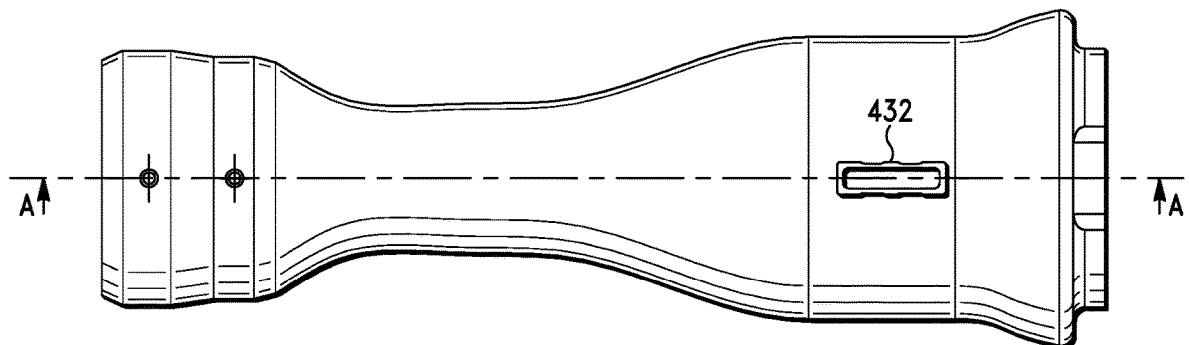

FIG. 28B is a side view of the handle shown in FIG. 28A.

Figure 28C:
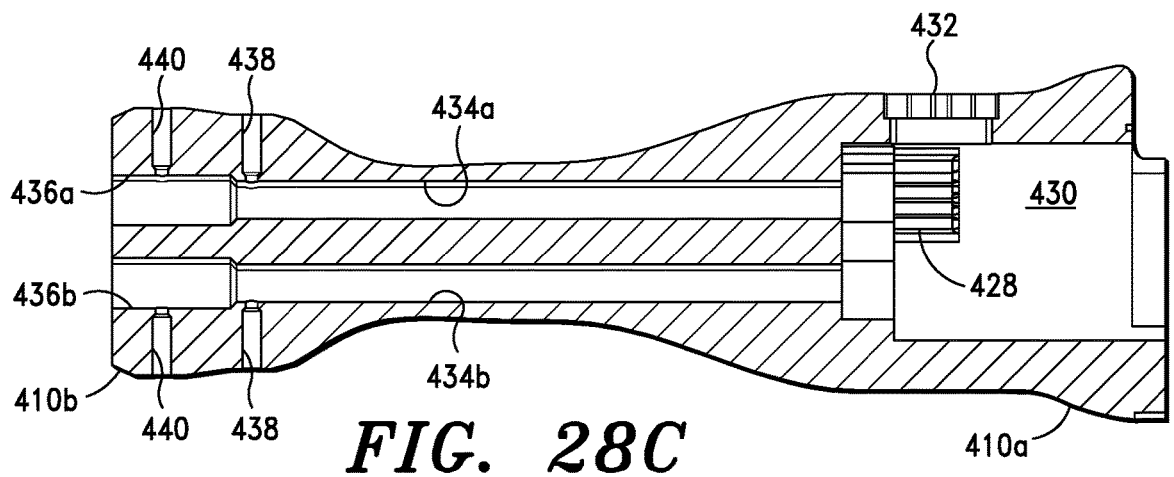

FIG. 28C is a cross-sectional view of the handle along line A-A in FIG. 28B.

Figure 28D:
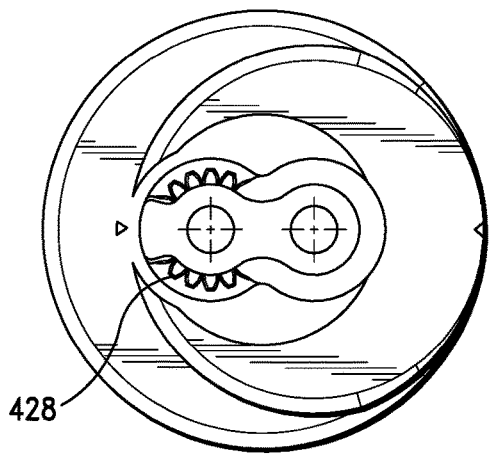

FIG. 28D is an end view from a first end of the handle shown in FIG. 28A.

Figure 28E:
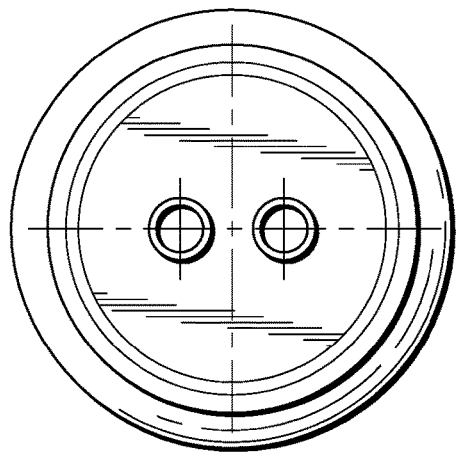

FIG. 28E is an end view from a second end of the handle shown in FIG. 28A.

Figure 29:
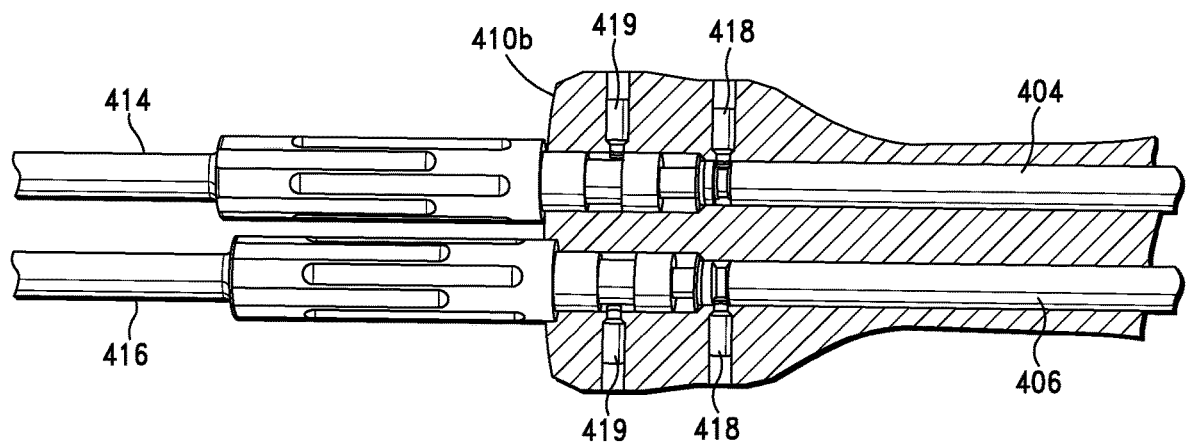

FIG. 29 is a perspective view of a portion of the operating instrument shown in FIG. 21A, illustrating the housing, the outer connection shafts, and the driving shafts with greater clarity.

Figure 30:
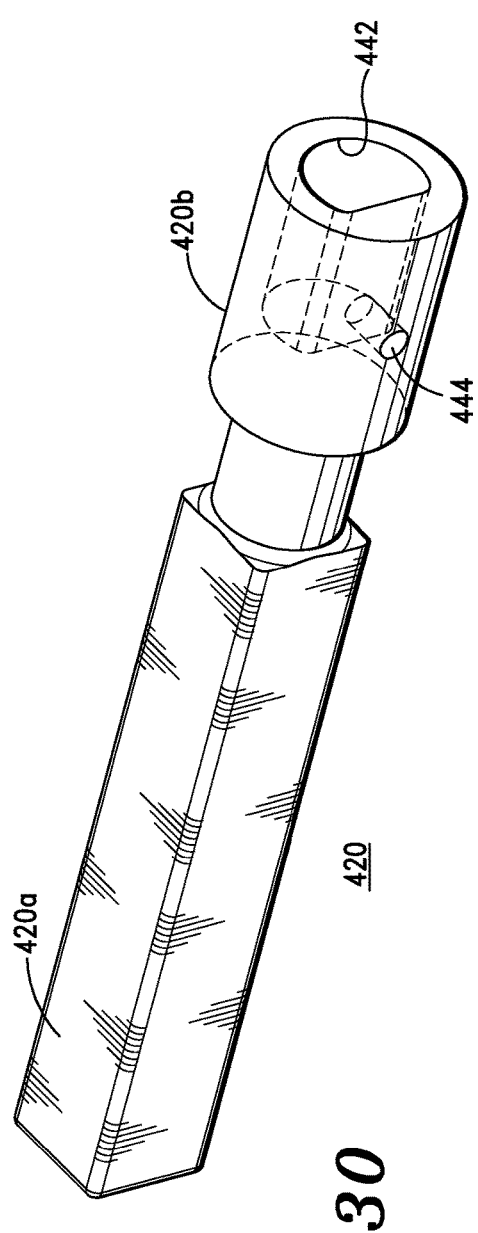

FIG. 30 is a perspective view of an exemplary adapter according to embodiments of the disclosure.

Figure 31:
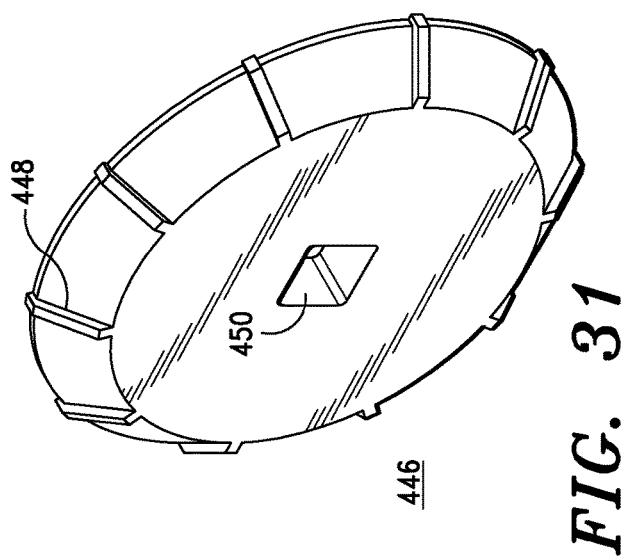

FIG. 31 is a perspective view of an exemplary dial according to embodiments of the disclosure.

Figure 32:
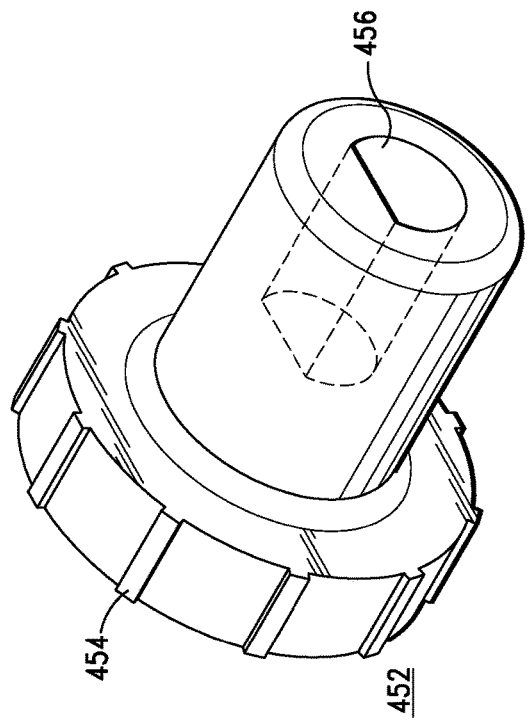

FIG. 32 is a perspective view of an exemplary dial according to embodiments of the disclosure.

DETAILED DESCRIPTION OF THE INVENTION

Figure 1:
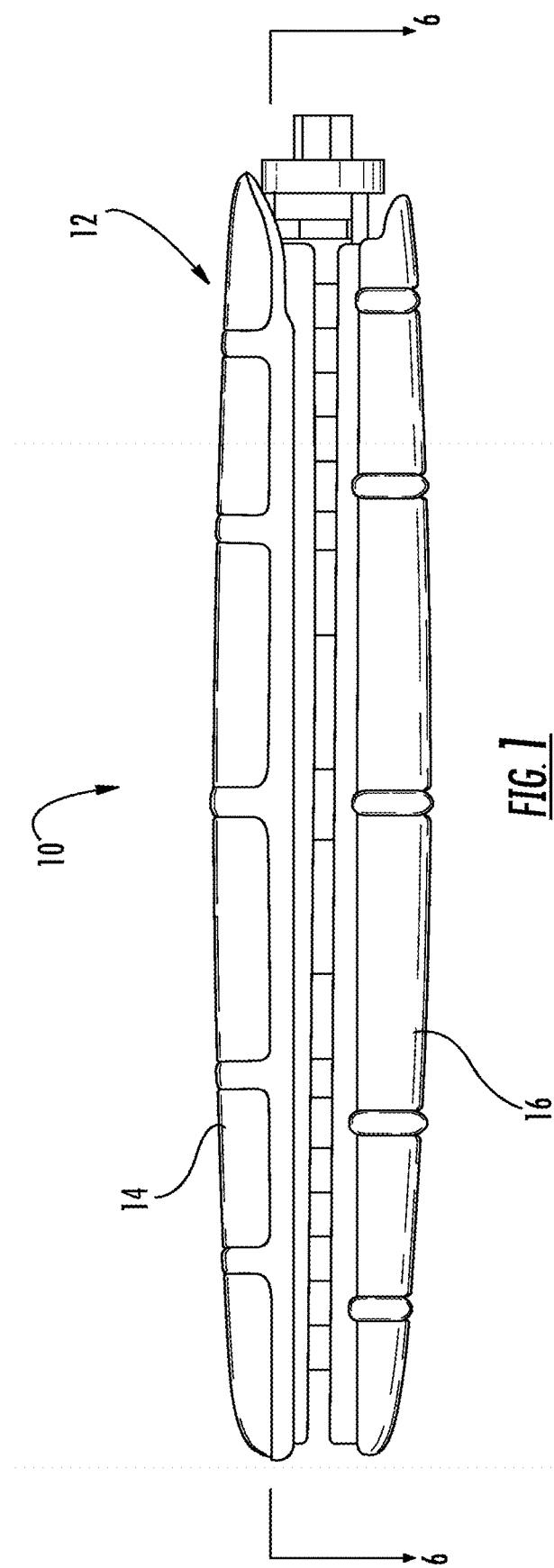
FIG. 1 is a view in side elevation from the side of the expandable shell device.
Figure 2:
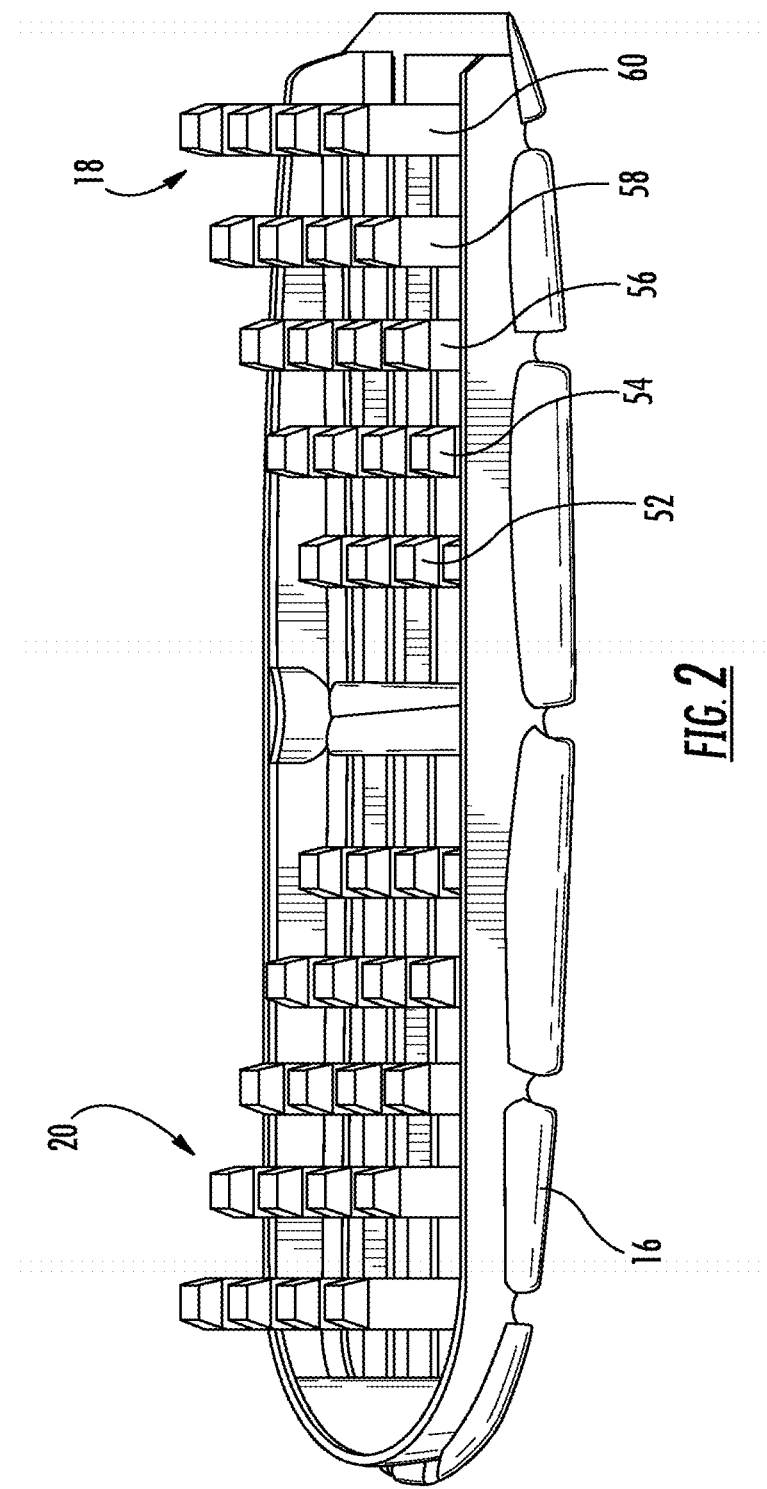
FIG. 2 is a perspective view of a bottom section of the expandable shell.
Figure 3:
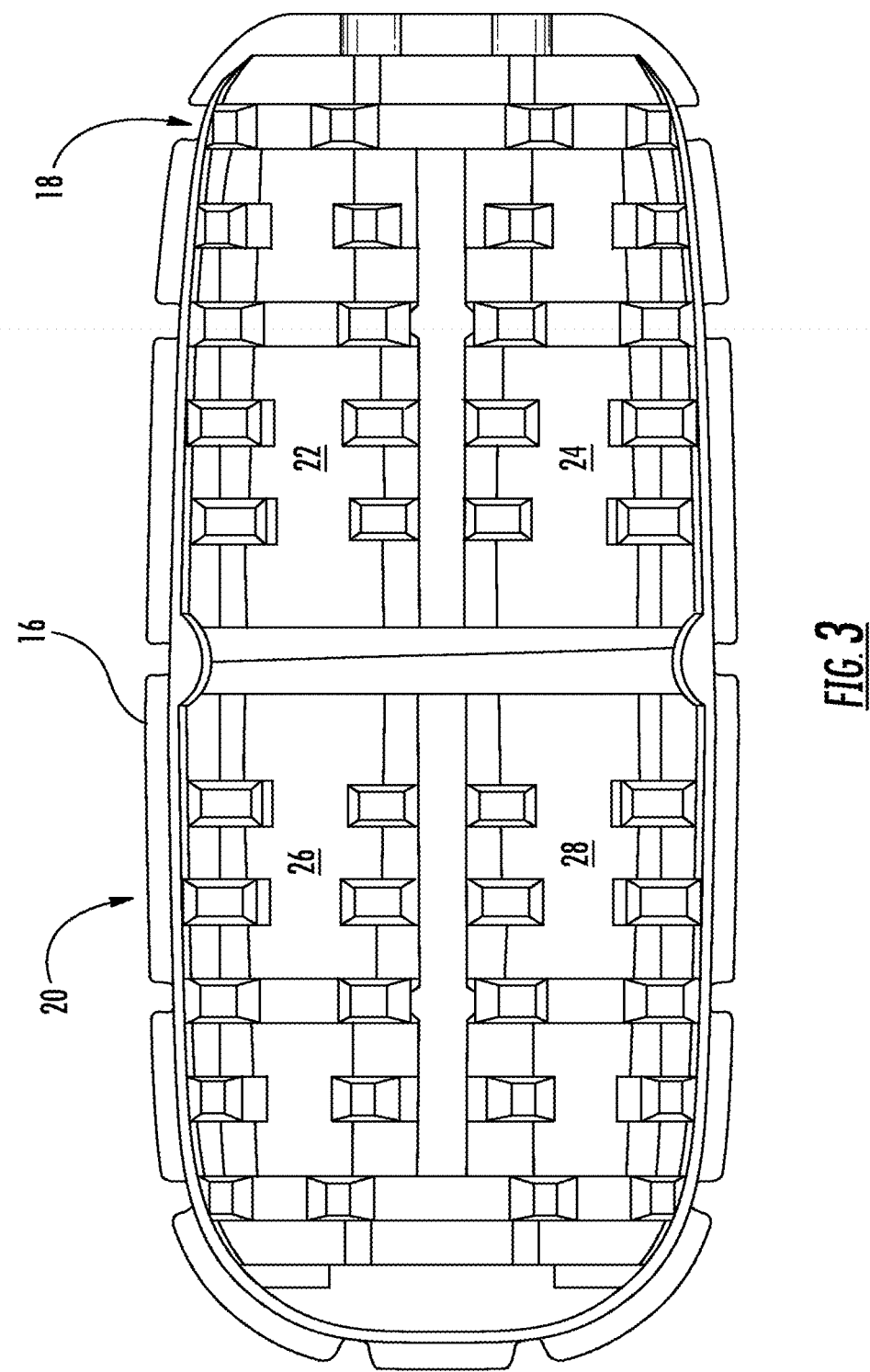
FIG. 3 is a top plan view of the bottom section of the expandable shell.
Figure 4:
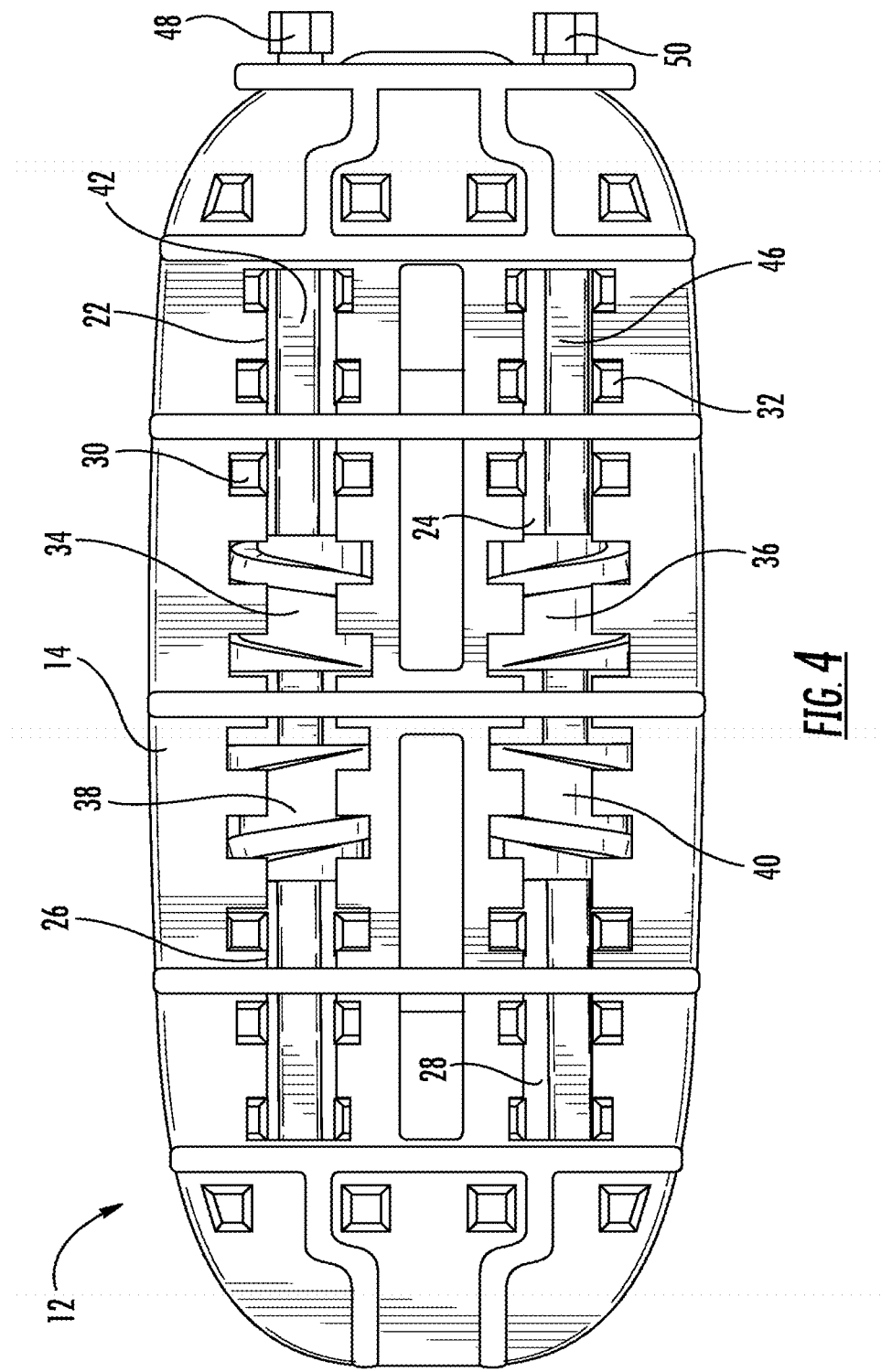
FIG. 4 is a top plan view of the expandable shell device.

With reference to the drawings figures, an interbody fusion body device is herein described, shown, and otherwise disclosed in accordance with various embodiments, including preferred embodiments, of the present invention. The interbody fusion device 10 is shown generally in FIG. 1. It is comprised of a housing 12 having a top shell 14 and a bottom shell 16. The overall housing may have a length of 50 mm and a width of 20 mm, as an example. The shell material may be comprised of a suitable material, such as titanium alloy (Ti-6AL-4V), cobalt chromium, or polyether ether ketone (PEEK). Other materials may be suitable that can provide sufficient compositional integrity and that have suitable biocompatible qualities. The interior of the shells are configured with a cascading step tracking 18 and 20 placed along their lateral edges. As shown in FIG. 2, step tracking 18 begins towards the midpoint of an inner surface of bottom shell 16 with successive track steps increasing in height as the tracking extends to a first end of bottom shell 16. Correspondingly, step-tracking 20 begins towards the midpoint of the inner surface of bottom shell 16 with successive track steps increasing in height as that portion of the tracking extends to a second opposite end of bottom shell 16. Step tracking 18 comprises dual track runs 22 and 24 while step tracking 20 comprises dual track runs 26 and 28 as shown in FIG. 3. Corresponding step tracking 30 and 32 is provided on top shell 14 as shown in FIG. 4. When the device is in its fully compressed state where top shell 14 lies adjacent to bottom shell 16, as shown in FIG. 1, step tracking 18 intermeshes with step tracking 30 and step tracking 20 intermeshes with step tracking 32.

Figure 5:
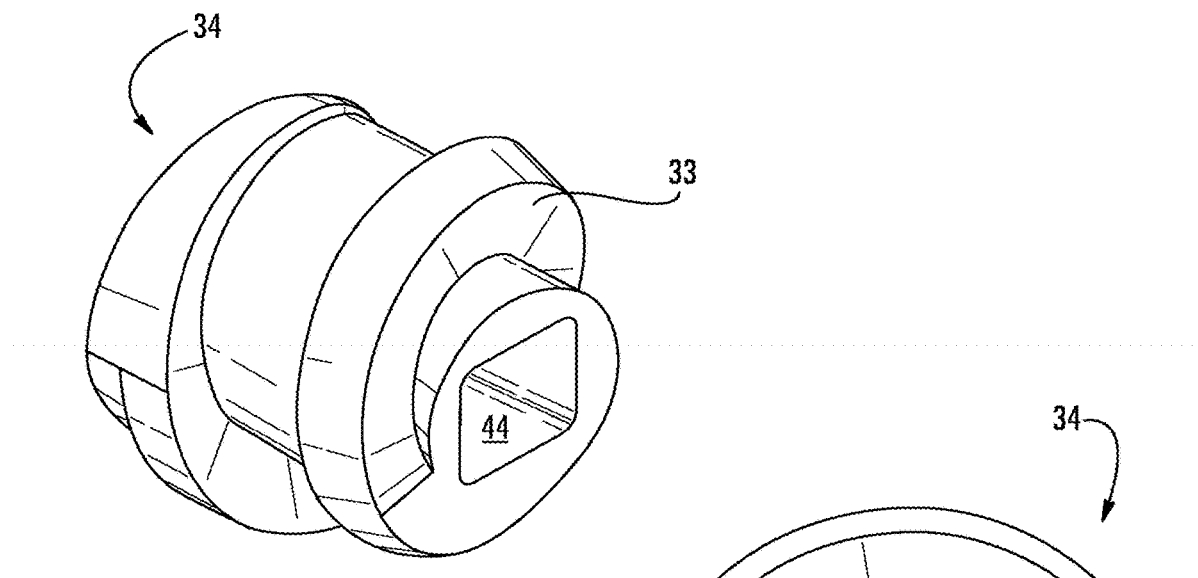
FIG. 5 is a perspective view of a tapered external helical threaded member.
Figure 5B:
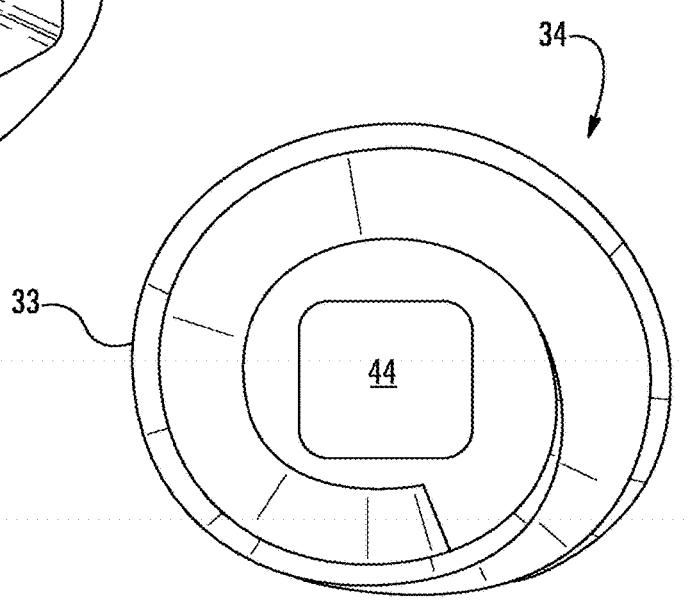
FIG. 5B is a view in side elevation from the front of the tapered external helical threaded member.
Figure 5A:
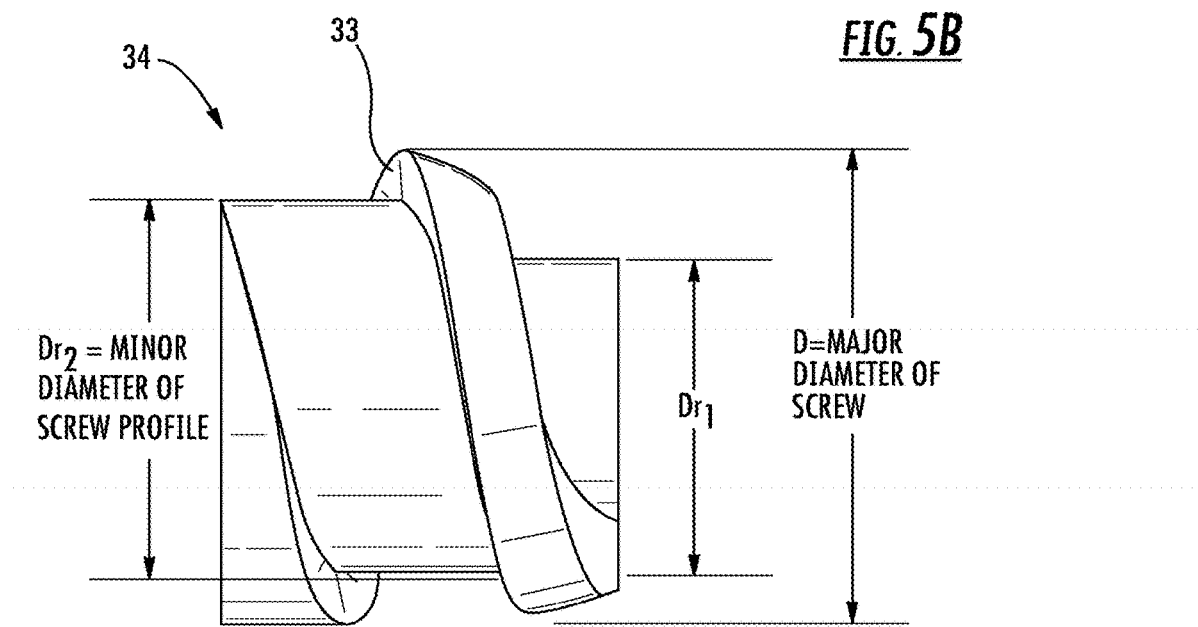
FIG. 5A is a view in side elevation from the side of the tapered external helical threaded member.

The respective track runs comprise a series of risers, or track steps, which are spaced apart to receive the threads of tapered external helical threaded members. The tapered external helical threaded members provide a wedging action for separating the top and bottom shell thereby increasing the height of the housing to effect expansion between the vertebral bodies in which the device is placed. As shown in FIG. 4, track run 22 receives tapered external helical threaded member 34, track run 24 receives tapered external helical threaded member 36, track run 26 receives tapered external helical threaded member 38, and track run 28 receives tapered external helical threaded member 40. Track run 22 aligns collinearly with track run 26 such that the travel of tapered external helical threaded members 34 and 38 within the respective track runs occurs within that collinear alignment. The thread orientation of tapered external helical threaded members 34 and 38 are opposite of each other such that their rotation will result in opposite directional movement with respect to each other. As shown in FIG. 4, a drive shaft 42 runs along the collinear span of track runs 22 and 26 and passes through tapered external helical threaded members 34 and 38. Shaft 42 has a square cross sectional configuration for engaging and turning the tapered external helical threaded members. As shown in FIG. 5, the central axial opening 44 of the tapered external helical threaded members are configured to receive and engage the shaft 42. Shaft 42 may alternatively comprise any shape for effectively creating a spline, such as a hexagonal shape, and central axial openings 44 may comprise a corresponding configuration for receiving that shape. As shaft 42 is rotated by its end 48 in a clockwise direction, tapered external helical threaded members 34 and 38 are rotated and their respective thread orientations cause the screws to travel apart from each other along track run 22 and track run 26, respectively. Correspondingly, as shaft 42 is rotated by its end 48 in a counter-clockwise direction, tapered external helical threaded members 34 and 38 are caused to travel towards each other along track run 22 and track run 26, respectively.

Similarly, track run 24 aligns collinearly with track run 28 such that the travel of tapered external helical threaded members 36 and 40 within the respective track runs occurs within that collinear alignment. The thread orientation of tapered external helical threaded members 36 and 40 are opposite of each other such that their rotation will result in opposite directional movement with respect to each other. Also, shaft 46 passes through and engages tapered external helical threaded members 36 and 40. However, the orientation of tapered external helical threaded members 36 and 40 is reversed from the orientation of tapered external helical threaded members 34 and 38. Under this orientation, as shaft 46 is rotated by its end 50 in a counter-clockwise direction, tapered external helical threaded members 36 and 40 are rotated and their respective thread orientations cause the screws to travel apart from each other along track run 24 and track run 28, respectively. Correspondingly, as shaft 46 is rotated by its end 50 in a clockwise direction, tapered external helical threaded members 36 and 40 are caused to travel towards each other along track run 24 and track run 28, respectively.

Figure 7A:
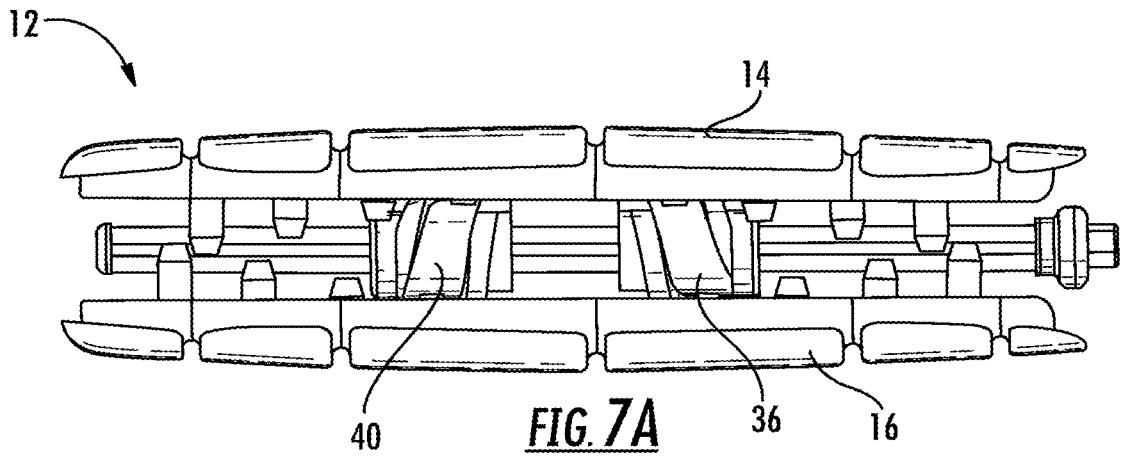
FIGS. 7A-7C are a series of views in side elevation of the device as it undergoes expansion.
Figure 7B:
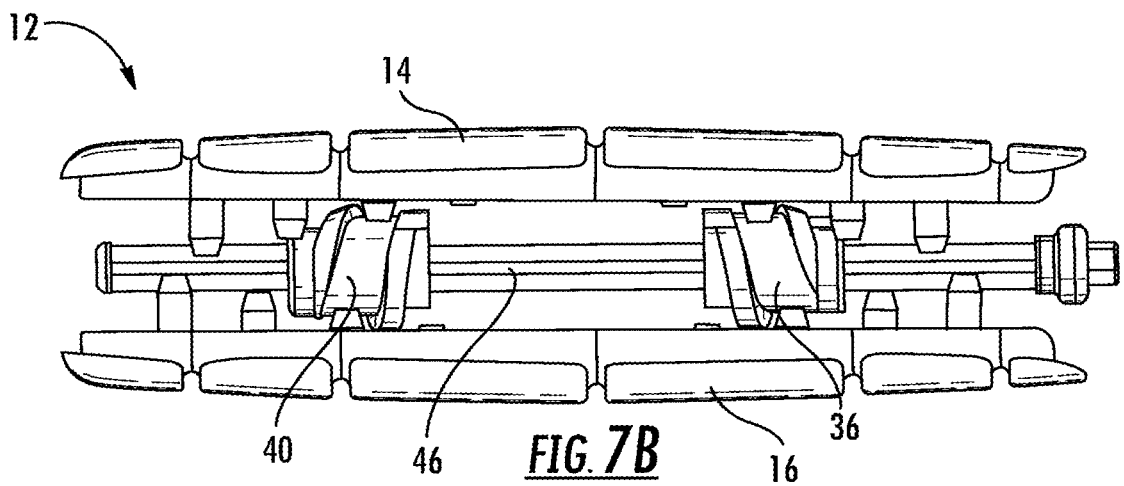
Figure 7C:
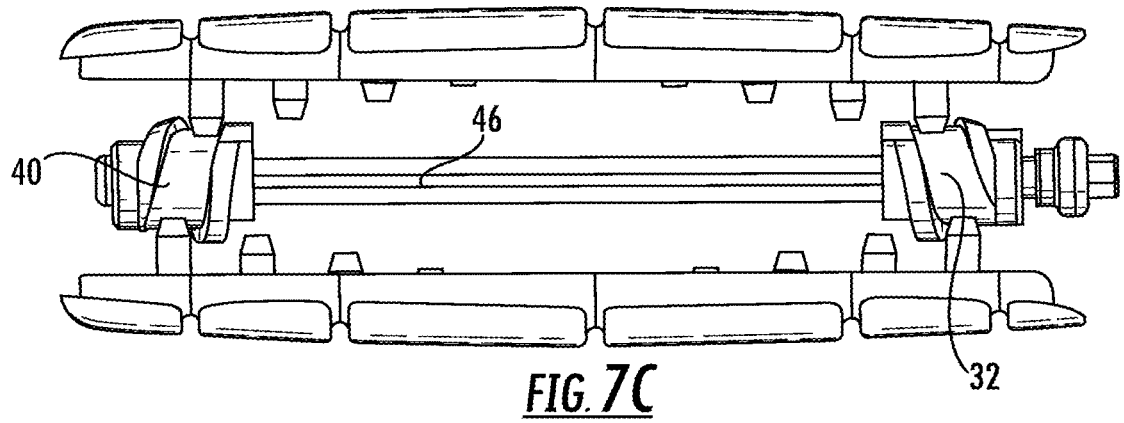

As shown in FIG. 2, the step tracking is configured with a cascading series of risers of increasing height. For example, each track run has risers 52-60 as shown for step tracking 18 in FIG. 2. As the thread of a tapered external helical threaded member travels into the gap between riser 52 and 54, the positional height of the tapered external helical threaded member body, as supported on risers 52 and 54, increases within the housing 12. As the tapered external helical threaded member continues to travel along the track run, its thread passes from the gap between risers 52 and 54 and enters the gap between risers 54 and 56 which raises the tapered external helical threaded member body further within housing 12 as it is supported on risers 54 and 56. As the tapered external helical threaded member continues its travel along the remainder of the step risers 58 and 60 its positional height increases further. As the positional height of the tapered external helical threaded member body increases, it urges top shell 14 apart from bottom shell 16 as shown in the series of FIGS. 7A-7C.

Figure 10:
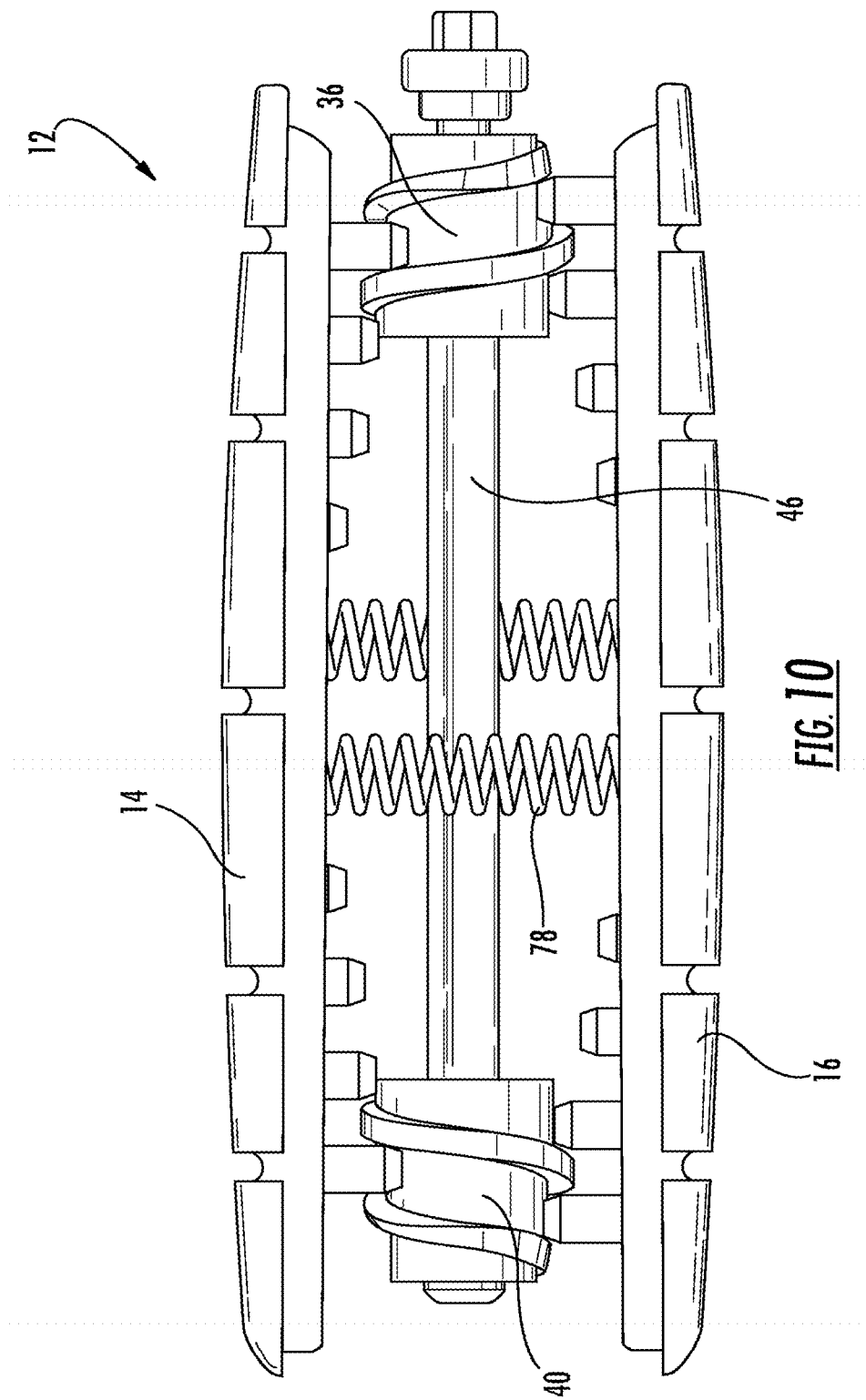
FIG. 10 is a side elevation view of the housing as expanded.

The combined effect of rotating the tapered external helical threaded members to cause their movement towards the outer ends of the respective track runs causes an expansion of the housing 12 as shown in FIG. 7. The fully expanded shell is shown in FIG. 10. The housing 12 may be contracted by reversing the movement of the tapered external helical threaded members such that they travel back along their respective track runs towards the midpoint of the housing. The housing will optimally provide expansion and contraction to give the implant device a height over a range of around approximately 7.8 mm to 16.15 mm in the present embodiment. The device of this embodiment of the invention can be adapted to provide different expansion dimensions.

Figure 8:
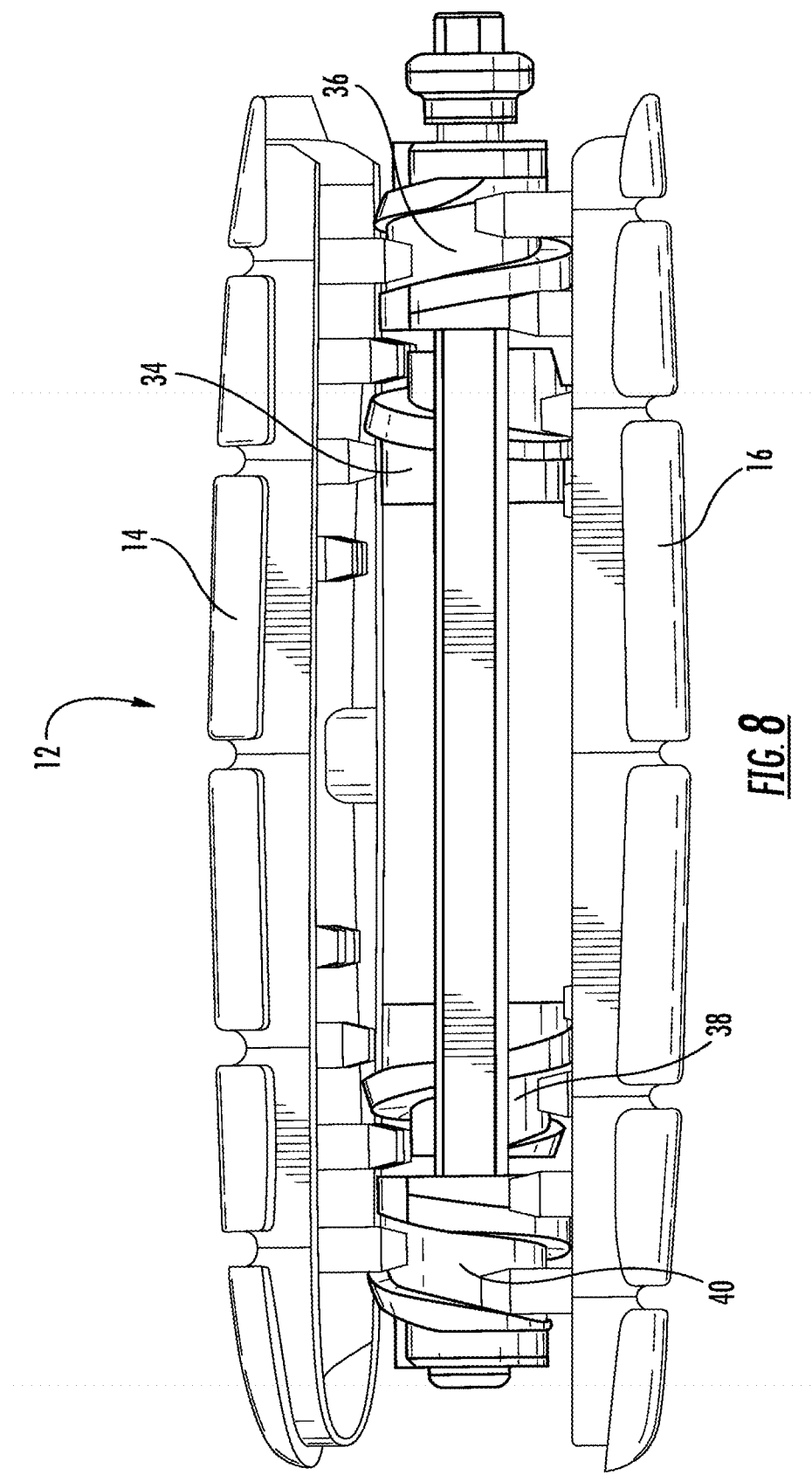
FIG. 8 is a view in side elevation of the device showing an expansion of the device to accommodate a lordotic effect.

The pairs of tapered external helical threaded members in each collinear dual track run may be rotated independently of the pair of tapered external helical threaded members in the parallel track run. In this arrangement, the degree of expansion of that portion of the housing over each collinear track run may be varied to adjust the lordotic effect of the device. As an example shown in FIG. 8, tapered external helical threaded members 36 and 40 have been extended to a particular distance along track run 24 and track run 28, respectively, causing the top shell 14 to separate from bottom shell 16 thereby expanding housing 12. Tapered external helical threaded members 34 and 38 have been extended to a lesser distance along parallel track run 22 and 26, respectively, causing that portion of the top shell over track runs 22 and 26 to separate from bottom shell to a lesser degree. The series of FIGS. 15A-15C show this effect where tapered external helical threaded members 36 and 40 are extended apart from each other in further increasing increments where the tapered external helical threaded members 34 and 38 maintain the same relative distance to each other.

In FIG. 15A, the respective positioning of the set of tapered external helical threaded members 36-40 is approximately the same as the set of tapered external helical threaded members 34-38 in their respective tracking. In this position, the top shell 14 is essentially parallel with bottom shell 16. In FIG. 15B, the set of tapered external helical threaded members 36-40 move further distally apart along their tracking as the set of tapered external helical threaded members 34-38 remains at their same position in FIG. 15A. In this setting, the lateral edge of top shell 14 along which tapered external helical threaded members 36 and 40 travel is moved higher with respect to the lateral edge of top shell 14 along which tapered external helical threaded members 34 and 38 travel, giving a tilt to top shell 14 with respect to bottom shell 16. In FIG. 15C, the set of tapered external helical threaded members 36-40 move even further distally apart along their tracking with respect to that of the set of tapered external helical threaded members 34-38, giving an even greater tilt to top shell 14 with respect to bottom shell 16. Through the independent movement of the respective tapered external helical threaded member sets, the device can achieve a lordotic effect of between 0° and 35° in the present embodiment. The device of this embodiment of the invention can be adapted to provide different lordotic tilt dimensions.

The tapered external helical threaded members have a configuration comprising a body profile that has an increasing minor diameter from $D_{r1}$ to $D_{r2}$ as shown in FIG. 5. The threads 33 have a pitch to match the spacing between the riser elements 52-60 in the tracking runs as shown in FIG. 4. Threads 33 can have a square profile to match the configuration between the risers, but other thread shapes can be used as appropriate. The increasing diameter and tapering aspect of the helical threaded members cause top shell 14 and bottom shell 16 to move apart as described above. The contact at the tops of the risers 52-60 is made at the minor diameter of the helical threaded member.

Figure 9B:
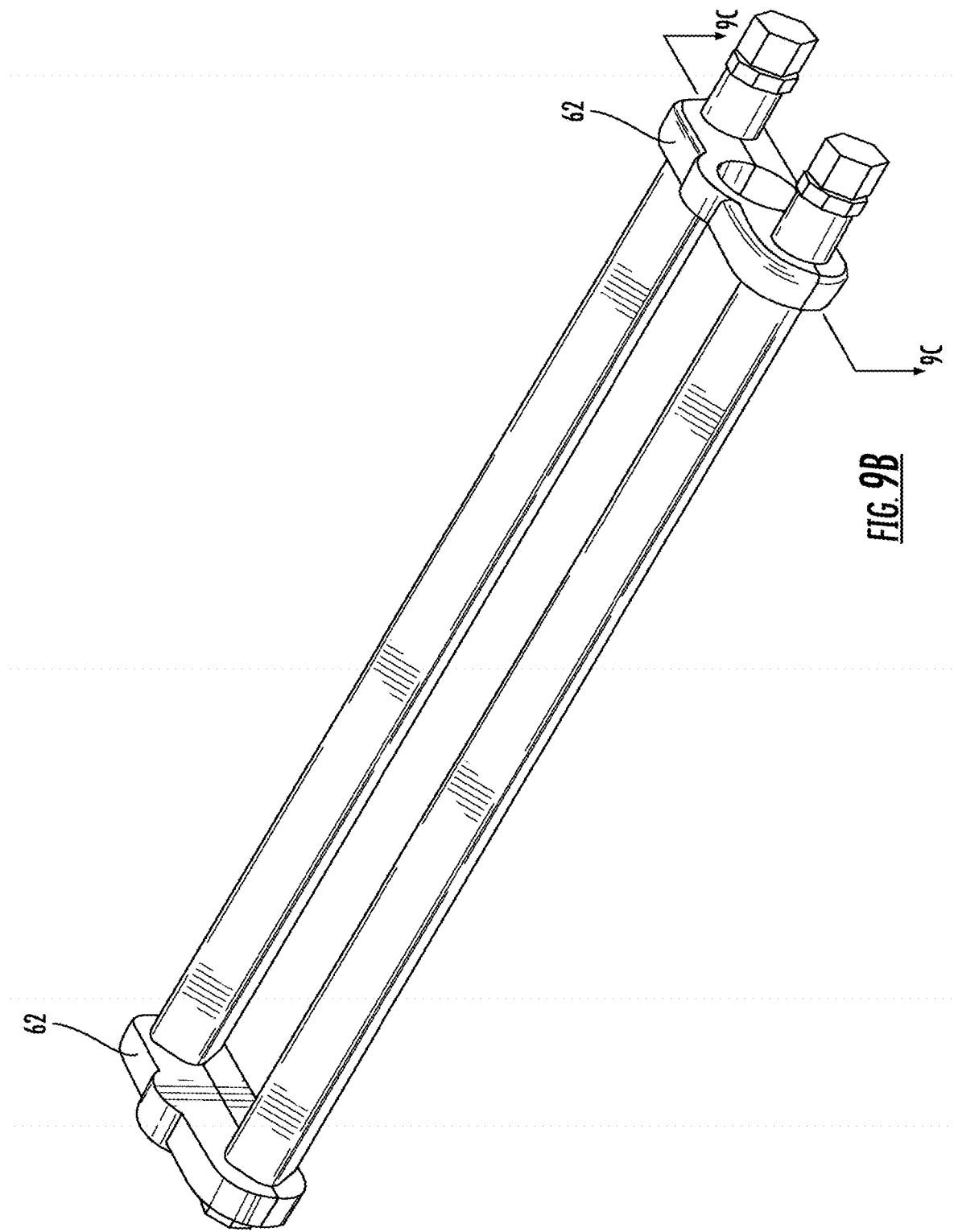
FIG. 9B is a perspective view of the drive shafts and thrust bearings.
Figure 9C:
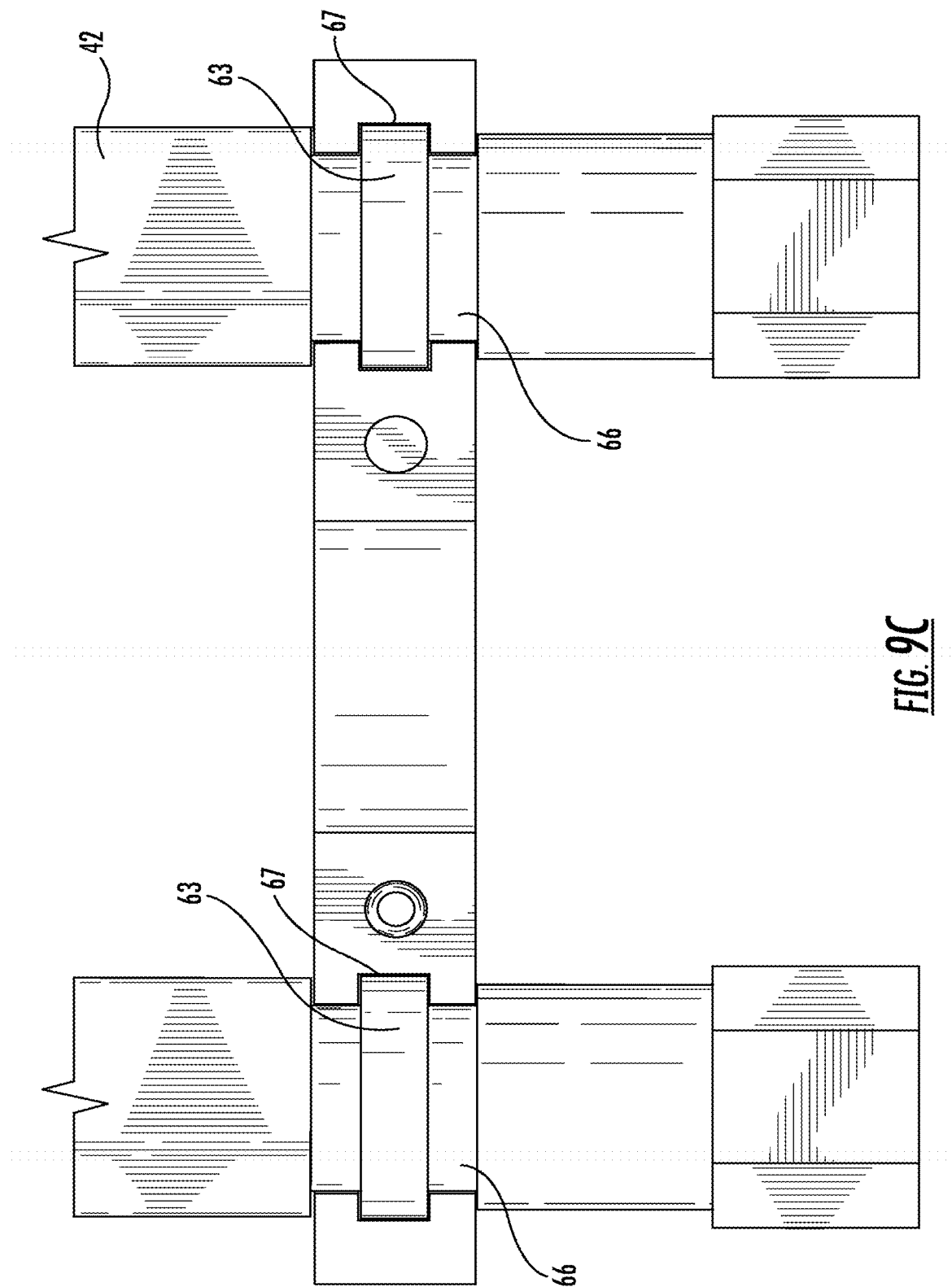
FIG. 9C is a top plan view in cross section of the area of engagement of the drive shafts with the thrust bearings.

Thrust bearings are provided to limit the axial direction motion of the drive shafts within shell 12. As shown in FIG. 9A, thrust bearing 62 comprises a two-piece yoke configuration that mate together and press-fit around ends of the shafts. The top part 64 of the thrust bearing yoke defines openings for receiving a round portion 66 of the shaft ends. In FIG. 9C, square shaft 42 has a rounded portion 66 of lesser diameter than the square portion of the shaft. A mating piece 65 of the thrust bearing engages with top part 64 to encircle the rounded portion 66 of drive shaft 42.

Figure 6:
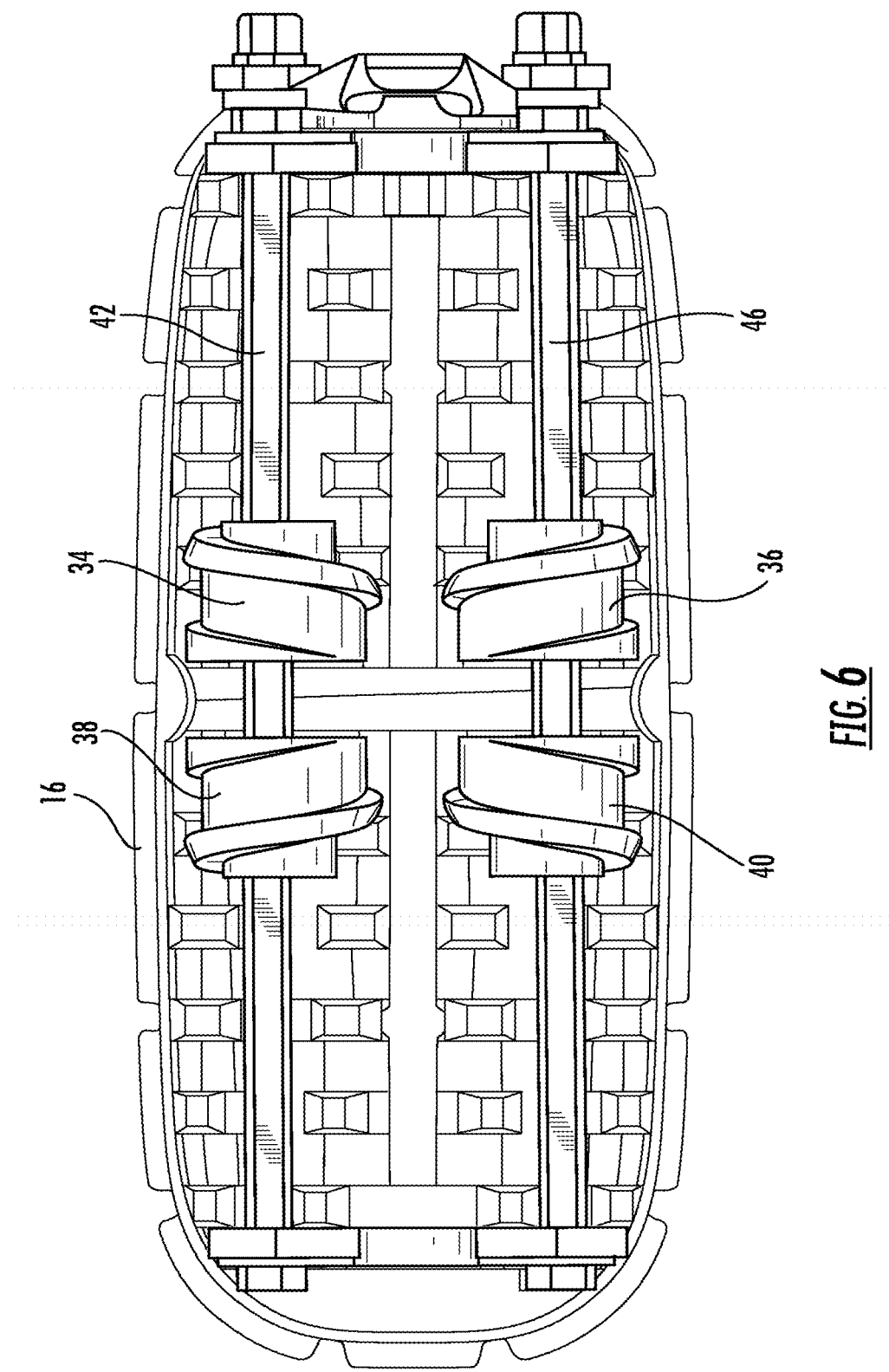
FIG. 6 is a cross-sectional view of the device taken along lines 6-6 in FIG. 1.

Pin elements 68 in the top portion 64 and bottom portion 65 engages a corresponding hole 69 in the mating piece to provide a press fit of the thrust bearing around the shaft. Journal grooves 67 can also be provided in thrust bearing 62. Shaft 42 can have an annular ridge 63 around its rounded portion 66 which is received in journal groove 67 as shown in FIG. 9C. A thrust bearing is provided at each end of the drive shafts as shown in FIG. 9B. As shown in FIG. 6, the thrust bearings restrict the axial movement of the drive shafts in the housing.

Figure 12A:
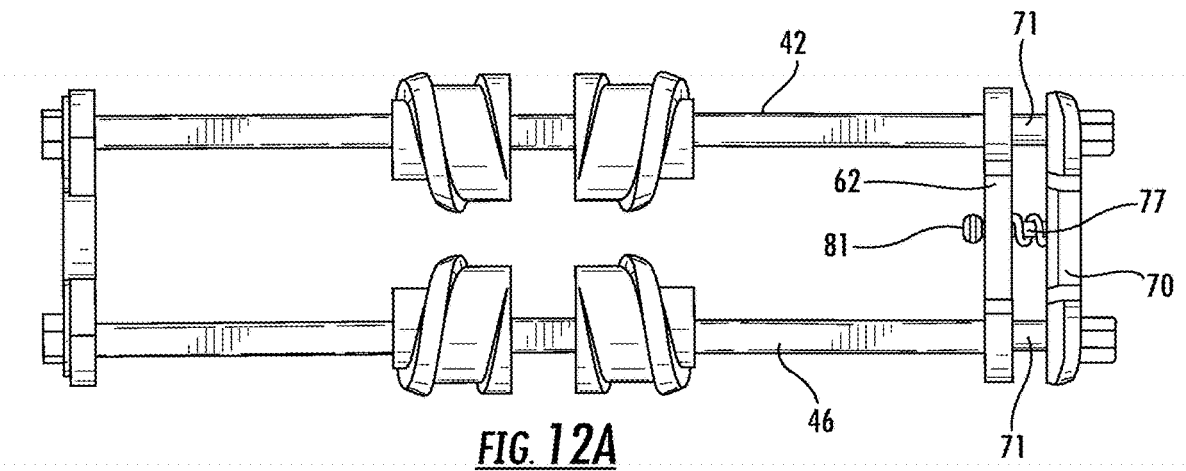
FIG. 12A is a top plan view of the drive shafts disengaged by the locking mechanism.
Figure 12B:
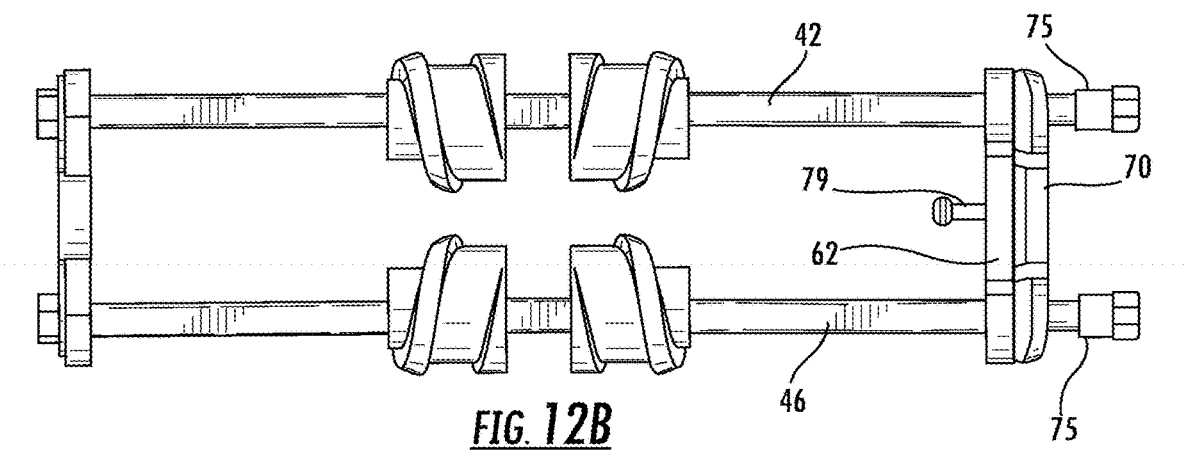
FIG. 12B is a top plan view of the drive shafts engaged by the locking mechanism.
Figure 13A:
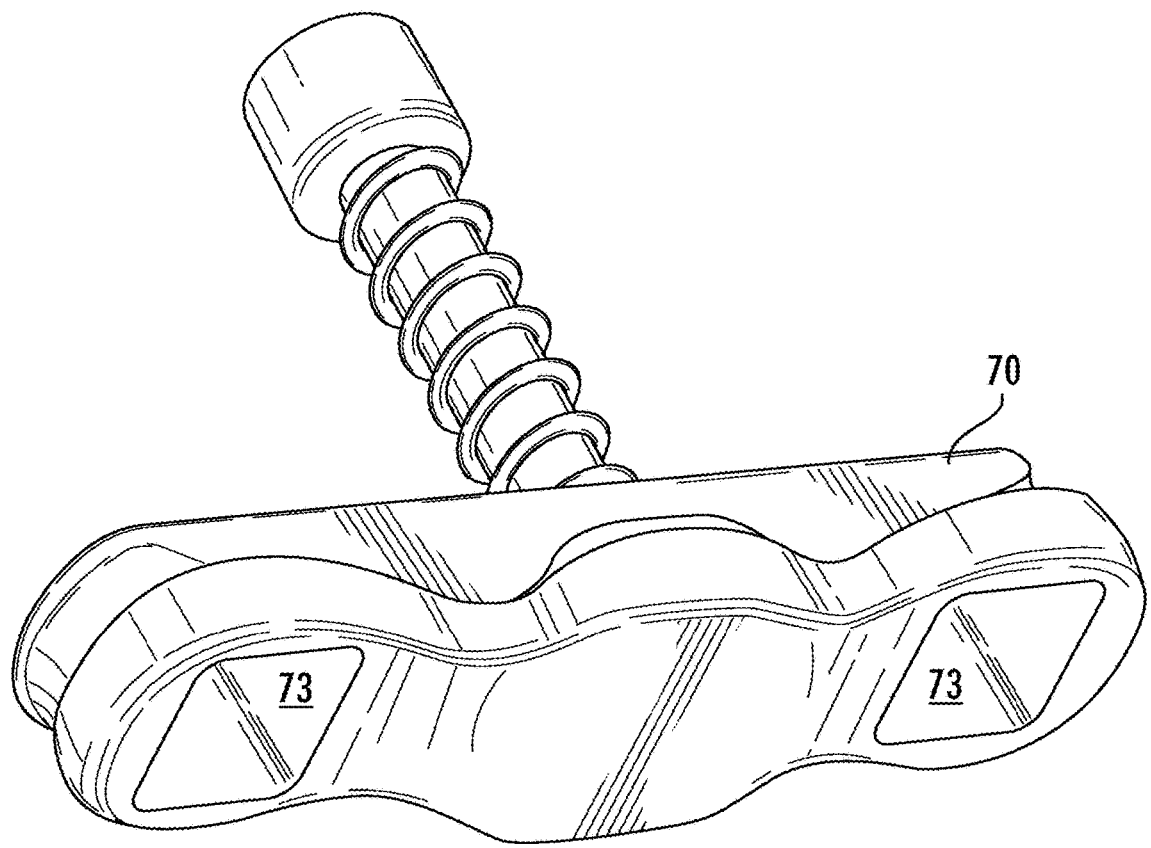
FIG. 13A is a perspective view of the locking mechanism.
Figure 13B:
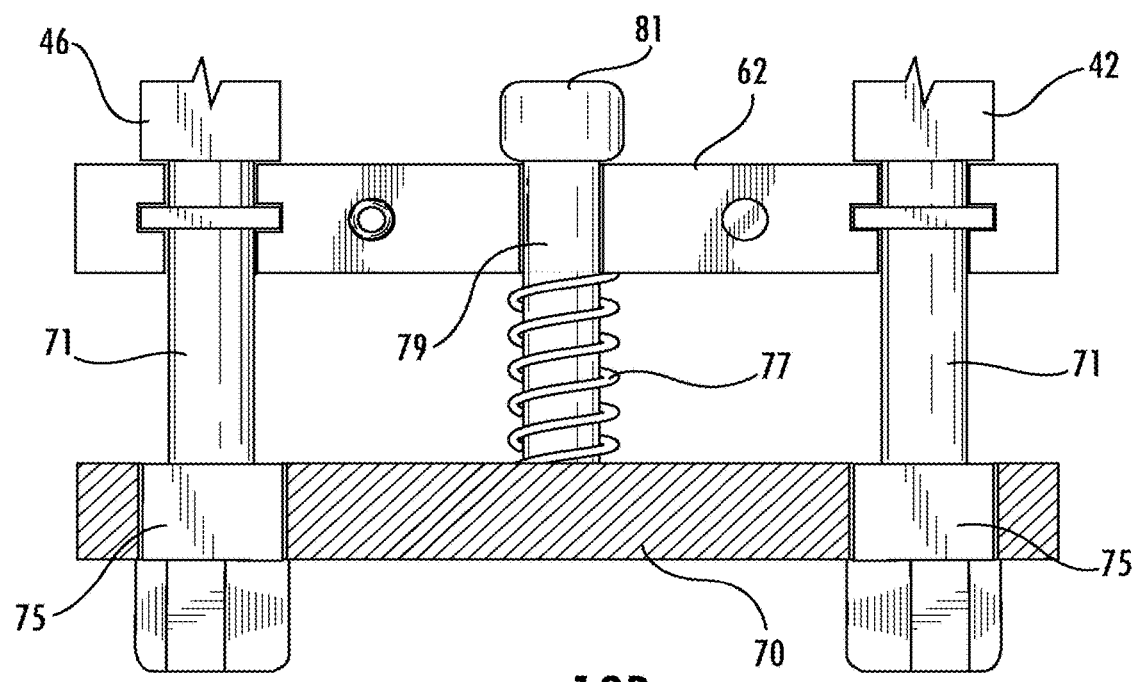
FIG. 13B is a top plan cross sectional view of the drive shafts disengaged by the locking mechanism.
Figure 13C:
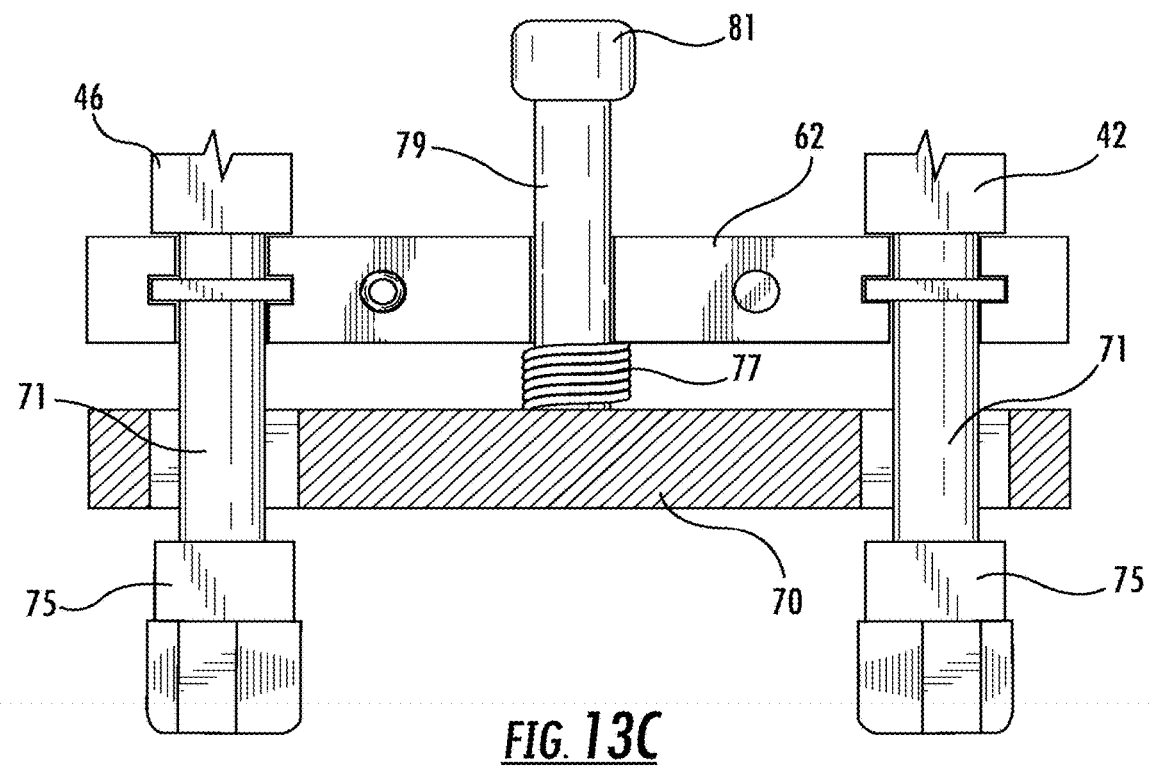
FIG. 13C is a top plan cross sectional view of the drive shafts engaged by the locking mechanism.

A safety lock is provided at the proximal end of the device for preventing unintended rotation of the shafts. As shown in FIGS. 12A and 12B, safety lock member 70 is provided for engagement with the proximal ends of drive shafts 42 and 46. The openings 73 in safety lock member 70 are configured with the shape of the cross-sectional configuration of the drive shafts (see FIG. 13A). A portion of the drive shafts has a narrowed, rounded configuration 71 such that the drive shaft can rotate freely while the rounded portion of the shaft is in alignment with the safety lock member openings 73 (see FIG. 13C). FIG. 12B shows this relationship among the safety lock member 70, thrust bearing 62 and drive shafts 42 and 46. When the non-narrowed portions 75 of the shafts are placed in alignment with the safety lock member openings 73, then rotation of the shafts is prevented (see FIG. 13B). FIG. 12A shows this relationship among the safety lock member 70, thrust bearing 62 and drive shafts 42 and 46. A compression spring 77 can be placed between thrust bearing 62 and safety lock member 70 to urge safety lock member back over the square portion 75 of the drive shafts. FIG. 12B shows a lock disengagement when the safety lock member 70 is pushed forward out of alignment with the square portions 75 and placed in alignment with the rounded portions 71 of shafts 42 and 46. Post 79 can be disposed between safety lock member 70 and thrust bearing 62 on which compression spring 77 can be positioned. Post 79 can be fixedly connected to safety lock member 70 and an opening can be provided in thrust bearing 62 through which post 79 can slide. Post 79 is provided with head 81 to limit the backward movement of safety lock member 70 from the compressive force of spring 77.

The interaction of the tapered external helical threaded members with the step tracking contributes to self-locking under a power screw theory. In considering the variables for promoting a self-locking aspect of the tapered threaded members, certain factors are relevant. In particular, those factors include the coefficient of friction of the materials used, such as Ti-6Al-4V grade 5, the length of pitch of the helical threads and the mean diameter of the tapered member. The following equation explains the relationship among these factors in determining whether the tapered external helical threaded members can self-lock as it travels along the step tracking:

$$T_R = \frac{Fd_m}{2} \left( \frac{l + \pi f d_m \sec\alpha}{\pi d_m - fl \sec\alpha} \right)$$

The above equation determines the torque necessary to apply to the drive shafts engaging the tapered external helical threaded members for expanding the shell members.

This torque is dependent upon the mean diameter of the tapered external helical threaded members, the load (F) applied by the adjacent vertebral bodies, the coefficient of friction (f) of the working material, and the lead (l) or, in this embodiment, the pitch of the helical threading. All of these factors determine the required operating torque to transform rotational motion into a linear lift to separate the shell members in accomplishing expansion and lordosis.

The following equation describes the relationship among the factors relating to the torque required to reverse the tapered external helical threaded members back down the tracking:

$$T_R = \frac{Fd_m}{2}\left(\frac{\pi f d_m - l}{\pi d_m + fl}\right)$$

Under this equation, the torque required to lower the tapered external helical threaded members ($T_L$) must be a positive value. When the value of ($T_L$) is zero or positive, self-locking of the tapered external helical threaded members within the step tracking is achieved. If the value of ($T_L$) falls to a negative value, the tapered external helical threaded members are no longer self-locking within the step tracking. The factors that can contribute to a failure to self-lock include the compressive load from the vertebral bodies, the pitch and mean diameter of the helical thread not being adequately great, and an insufficient coefficient of friction of the material. The condition for self-locking is shown below:

$$\pi f d_m > l$$

Under this condition, it is necessary to select an appropriate combination of sufficient mean diameter size of the tapered member, along with the product material being a greater multiple than the lead or pitch in this particular application so that the tapered members can be self-locking within the step tracking. Based upon average values with a patient lying on their side, the lumbar vertebral body cross sectional area is around 2239 mm$^2$ and the axial compressive force at that area is 86.35 N. With the working material selected to be Ti-6Al-4V, the operating torque to expand shell housing 12 between L4-L5 of the vertebral column is around 1.312 lb-in (0.148 N-m), and the operating torque to contract shell housing 12 between L4-L5 of the vertebral column is around 0.264 lb-in (0.029 N-m).

Figure 11A:
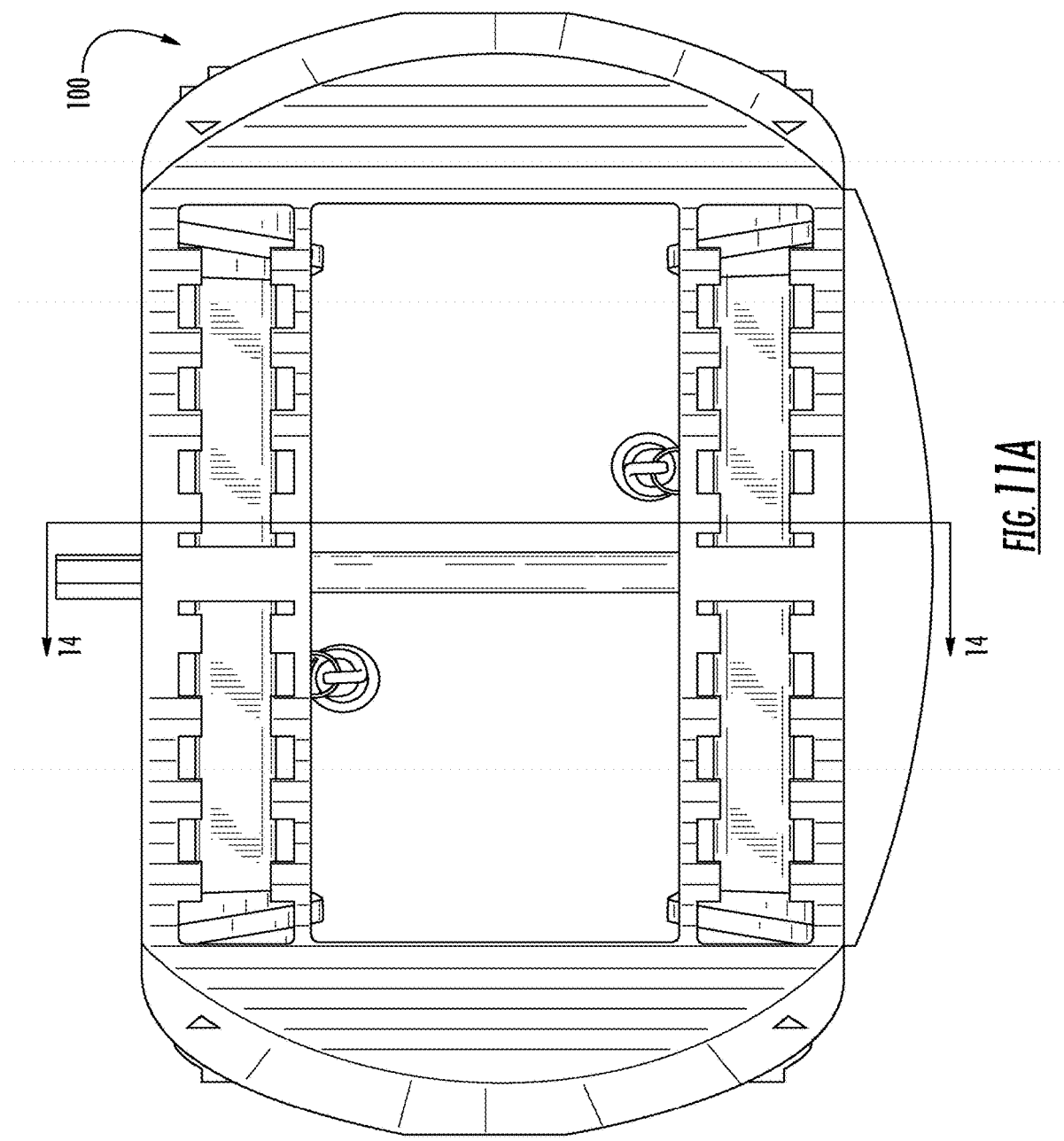
FIG. 11A is a top plan view of another embodiment of the device.

Alternate embodiments of the expandable shell housing provide for different surgical approaches. FIG. 11A shows housing 100 for use where a surgeon approaches the lumbar area from an anterior aspect of the patient. The general configuration of the tracking runs for this embodiment is similar to that for device 10, but the drive shafts for moving the tapered external helical threaded members are applied with a torque delivered from a perpendicular approach. For this, a dual set of worm gears 102 and 104 respectively transfer torque to drive shafts 106 and 108 as shown in FIG. 14.

FIG. 11B shows housing 200 for use where a surgeon approaches the lumbar area from a transforaminal aspect of the patient. The general configuration of the tracking runs for this embodiment is also similar to that for device 10, but the torque is applied to the drive shafts from an offset approach. For this, a dual set of bevel gears (not shown) may be used to transfer torque to drive shafts 206 and 208.

Housing 12 is provided with numerous niches and open areas in its surface and interior regions to accommodate the storage of bone grafting material. The interstitial spaces between the risers of the cascading step tracking also offers areas for receiving bone-grafting material. A membrane can be provided as a supplement around housing 12 to help maintain compression on the top and bottom shells and to hold in bone grafting material. Tension spring elements 78 can be provided to hold together top member 14 and bottom member 16 as shown in FIG. 10. These elements may also serve to provide an initial tension force in the direction opposite of the expansion against the interbody fusion device. This allows the tapered external helical threaded members to climb the risers in the event that contact between the outer shells and the vertebral bodies is not yet made.

Accordingly, this embodiment of the interbody fusion device of the instant invention is capable of expansion to provide support between vertebral bodies and accommodate the load placed on that region. Furthermore, the inventive interbody fusion device is capable of achieving a configuration that can provide an appropriate lordotic tilt to the affected region. The device, therefore, provides a significant improvement with regards to patient-specific disc height adjustment.

The device is provided with a tool for operating the interbody fusion device as it is adjusted in situ in a patient's spine. The operating tool 300 is shown generally in FIG. 16 and comprises a handle member 302, a gear housing 304 and torque rod members 306 and 308. The torque rod members connect to the drive shafts of expandable shell 12. One embodiment for connecting the torque rod members to the drive shafts of expandable shell 12 is shown in FIG. 17. In this arrangement, ends 48 and 50 of drive shafts 42 and 46 can be provided with a hex-shaped head. The ends of torque rod members 306 and 308 can be provided with correspondingly shaped receivers for clamping around ends 48 and 50.

Within the gear housing 304, handle member 302 directly drives torque rod member 308. Torque rod member 308 is provided with spur gear member 310 and torque rod member 306 is provided with spur gear member 312. Spur gear 312 is slidably received on torque rod member 306 and can move in and out of engagement with spur gear 310. Spur gear lever 314 engages with spur gear 312 for moving spur gear 312 into and out of engagement with spur gear 310. When torque rod member 308 is rotated by handle 302, and spur gear 312 is engaged with spur gear 310, rotation is translated to torque rod member 306. In this condition, torque rod member 308 rotates drive shaft 46 simultaneously with torque rod member 306 rotates drive shaft 42 to effect expansion of shell 12 as shown in FIGS. 7A-7C. Spur gear 312 can be moved out of engagement with spur gear 310 by retracting spur gear lever 314 as shown in FIG. 20. With spur gear 312 out of engagement with spur gear 310, rotation of handle 302 only turns torque rod member 308. In this condition, torque rod member 308 rotates drive shaft 46 solely and drive shaft 42 remains inactive to effect the tilt to the top member of shell 12 as shown in FIG. 8 and FIGS. 15A-15C to achieve lordosis.

To achieve expansion of the device in the described embodiment, the operator will turn handle member 302 clockwise to engage torqueing. This applied torque will then engage the compound reverted spur gear train composed of spur gear members 310 and 312. This series of gears will then spin torque rod members 306 and 308 in opposite directions of each other. Torque rod member 308 (in alignment with handle member 302) will spin clockwise (to the right) and torque rod member 306 will spin counterclockwise (to the left). The torque rod members will then rotate the drive shafts of interbody fusion device 12 expanding it to the desired height.

To achieve lordosis the operator will move the spur gear lever 314 back towards handle member 302. By doing so spur gear 312 connected to torque rod member 306 is disengaged from the overall gear train, which in turn will disengage torque rod member 306. As a result, torque rod member 308 will be the only one engaged with the interbody fusion device 12. This will allow the operator to contract the posterior side of the implant device to create the desired degree of lordosis.

Referring to FIGS. 21-32, various embodiments of a surgical operating tool or instrument according to the disclosure will now be described.

FIG. 21A is a cutaway perspective view of an exemplary operating tool or instrument according to embodiments of the disclosure. FIG. 21B is an exploded perspective view of the operating tool or instrument shown in FIG. 21A. As shown, the exemplary operating tool 400 in general comprises a handle 402, driving shafts 404, 406, a gear assembly 408, and optionally outer connection or tubular shafts 414, 416. The gear assembly 408 may be received in a housing 410. The driving shafts 404, 406 and optionally the outer tubular shafts 414, 416 may be rotatably secured to the housing 410.

The handle 402 may be any suitable handle that a user can apply torque to the driving shafts 404, 406. The handle 402 can be shaped in various configurations including I-shaped or T-shaped configurations. The handle 402 may be a bi-directional ratchet handle which can apply torque by rotating both clockwise and counterclockwise. The handle 402 may be a torque limiting ratchet handle which can limit the torque applied by the user so that damage to a workpiece (not shown) does not take place. In some embodiments, the workpiece is an expandable and adjustable spinal implant device described above in conjunction with FIGS. 1-15, and the handle 402 is a bi-directional torque limiting ratchet handle to effect expansion, contraction, and/or tilt of the spinal implant device. Torque limiting ratchet handles are commercially available for example from Bradshaw Medical, Inc. in Kenosha, Wis.

The driving shafts 404, 406 may include a first driving shaft 404 and a second driving shaft 406. The first driving shaft 404 may be operably connected with and rotated by the handle 402. The second driving shaft 406 may be operably coupled with the first driving shaft 404 or decoupled from the first driving shaft 404 via the gear assembly 408 to be described in greater detail below. When the second driving shaft 406 is operably coupled with the first driving shaft 404, a first operating mode is provided wherein the handle 402 can rotate both the first driving shaft 404 and the second driving shaft 406. When the second driving shaft 406 is decoupled from the first driving shaft 404, a second operating mode is provided wherein the handle 402 rotates solely the first driving shaft 404.

The first and second driving shafts 404, 406 may each include a first portion 404a, 406a received in the housing 410 when assembled and a second portion 404b, 406b extending out of the housing 410. The first and second driving shafts 404, 406 may be rotatably secured to the housing 410 via screws 418, or keys, pins or the like to be described in greater detail below. The first and second driving shafts 404, 406 may have a substantially same length and cross-sectional geometry along the length. Alternatively, the first and second driving shafts 404, 406 may have different lengths and cross-sectional geometries. The first driving shaft 404 may be connected with the handle 402 via an adapter 420 to be described in greater detail below. Alternatively, the first driving shaft 404 may extend its length out of the housing 410 to connect with the handle 402.

FIGS. 22A-22C illustrate an exemplary driving shaft which can be used as the first and/or the second driving shaft 404, 406. As shown, the exemplary driving shaft 404 may include a first portion 404a and a second portion 404b. When the operating tool 400 is assembled, the first portion 404a may be received in the housing 410 and the second portion 404b may extend out of the housing 410. The first portion 404a and the second portion 404b may be integrally machined as a single component, or alternatively, separately machined and then assembled. The first and second portions 404a, 404b may be generally cylindrically shaped and have a diameter same as or different from each other.

The first portion 404a of the driving shaft 404 may include a potion 404d at the proximal end configured to receive a gear member, an adapter, or a dial to be described in greater detail below. For example, the portion 404d at the proximal end of the first portion 404a may include a flattened surface and a remaining cylindrical surface configured to receive a gear member, an adapter, or a dial having a channel, cutout, or aperture having a corresponding flattened surface and cylindrical surface. When a gear member, an adapter, or a dial is received on the portion 404d, the flattened surfaces prevent rotational movement of the gear member, adapter, or dial relative to the driving shaft 404. At the distal end, the first portion 404a of the driving shaft 404 may include an undercut or groove forming a rounded portion 404e with a reduced diameter. The undercut or groove provides space for crews, keys, pins, or the like to fit in or flush against the rounded portion 404e, thereby restricting the driving shaft 404 from axially moving or slipping out of the housing 410 while allowing the driving shaft 404 to freely rotate.

The second portion 404b extends from the first portion 404a and includes a workpiece-engaging tip 404c having features configured to engage a workpiece. As shown, the workpiece-engaging tip 404c has a torx or hexalobular configuration. Other suitable configurations or features known in the art may also be used to engage a workpiece having corresponding engaging features. The workpiece may be a spinal implant device described above in conjunction with FIGS. 1-15. The workpiece may also be other medical devices operable to expand, contract, or tilt by use of an operating tool.

Returning to FIGS. 21A-21B, the gear assembly 408 serves to couple the second driving shaft 406 with the first driving shaft 404 or decouple the second driving shaft 406 from the first driving shaft 404. In some embodiments, the gear assembly 408 may also lock the second and first driving shafts 406, 404 so that rotation of the first and second driving shafts 404, 406 are prohibited. As shown, the gear assembly 408 may include a first gear member 408a received on the first driving shaft 404, a second gear member 408b received on the second driving shaft 406, and a lever member 408c operable to place the second gear member 408b into and out of engagement with the first gear member 408a.

The first gear member 408a may be fixedly secured to the first driving shaft 404 via screws, keys, pins or the like. The second gear member 408b may be slidably received on the second driving shaft 406. The lever member 408c may be coupled to the second driving shaft 406 configured to move the second gear member 408b along the second driving shaft 406, thereby allowing the second gear member 408b to engage the first gear member 408a, to disengage the first gear member 408a, or to be locked in a locked position to be described in greater detail below. FIG. 23 depicts an exemplary lever member 408c which can be used in the operating tool 400. As shown, the lever member 408c may include a first annular ring 422a and a second annular ring 422b spaced apart e.g. by a generally U-shaped structure 424 coupled with a bar member 426. When assembled, the first and second rings 422a, 422b of the lever member 408c are slidably received on the second driving shaft 406 and the bar member 426 protrudes out of the housing 410. The second gear member 408b, which may be slidably received on the second driving shaft 406, is retained between the first and second annular rings 422a, 422b, and moved by the bar member 426.

FIGS. 24, 25, and 26 illustrate with greater clarity the gear assembly 408 in the housing 410. In FIG. 24, the lever member 408c is placed in a proximal or first position, which allows the second gear member 408b to engage with the first gear member 408a, thereby operably coupling the second driving shaft 406 with the first driving shaft 404. When the second driving shaft 406 is operably coupled with the first driving shaft 404, a rotation of the first driving shaft 404 by the handle 402 causes a rotation of the second driving shaft 406, providing a first operating mode wherein e.g. an expandable spinal implant device can be expanded or contracted. In FIG. 25, the lever member 408c is placed in a distal or second position, which allows the second gear member 408b to disengage the first gear member 408a, thereby decoupling the second driving shaft 406 from the first driving shaft 404. When the second driving shaft 406 is decoupled from the first driving shaft 404, the handle 402 rotates solely the first driving shaft 404 whereas the second driving shaft 406 becomes inactive, providing a second operating mode wherein e.g. a spinal implant device can be tilted.

In some embodiments, the lever member 408c may be placed in a third position where the second and first gear members 406, 404 are locked in the housing 410 and rotation of the first and second driving shafts 404, 406 are prohibited. In FIG. 26, the lever member 408c is placed in the middle between the proximal and distal positions, allowing the second gear member 408b to engage both the first gear member 408a and a teeth-like configuration 428 built in the housing 410, to be described in greater detail below. When the second gear member 408a is in contact or engaged with the teeth-like configuration 428, rotation of the second gear member 408b is restricted and as a result, rotation of the first gear member 408a is also restricted due to the engagement with the second gear member 408b. When the lever member 408c is placed in the third position, the operating tool 400 is locked wherein rotation of the first and second driving shafts 404, 406 is prohibited.

Returning to FIGS. 21A-21B, in some embodiments, the operating tool 400 may include outer connection or tubular shafts 414, 416 configured to connect the operating tool 400 to a workpiece such as a spinal implant device. The outer connection shafts 414, 416 may include a first tubular shaft 414 surrounding the second portion 404b of the first driving shaft 404 extending out of the housing 410, and a second tubular shaft 416 surrounding the second portion 406b of the second driving shaft 406 extending out of the housing 410. The first and second tubular shafts 414, 416 may be rotatably secured to the housing 410, to be described in greater detail below, so that the first and second tubular shafts 414, 416 are prevented from sliding out of the housing 410 while freely spinning or rotating independently of the rotation of the first and second driving shafts 404, 406 respectively.

FIGS. 27A-27C illustrate an exemplary tubular shaft which can be used as the outer connection shafts 414, 416. As shown, the exemplary tubular shaft 414 may be generally cylindrically shaped having an internal diameter greater than the outer diameter of the second portion of the driving shaft 404. The tubular shaft 414 may include a first end portion 414a configured to be rotatably secured to the housing 410 and a second end portion 414b having features configured to connect with a workpiece. A finger grip 414c, which may be machined as an integral part of the tubular shaft, may be provided to facilitate rotating or spinning of the tubular shaft in connecting with a workpiece. As detailed in FIG. 27C, the first end portion 414a of the tubular shaft 414 may include an undercut or groove forming a rounded portion 414d with a reduced diameter. When assembled, screws 419 (FIG. 21B), keys, pins, or the like may fit into the space in the undercut or groove or flush against the rounded portion 414d, thereby preventing the tubular shafts 414 from axially moving or sliding out of the housing while allowing the tubular shaft 414 to freely rotate. The second end portion 414b of the tubular shaft 414 may be provided with internal threads or other suitable features configured to connect with a workpiece such as a spinal implant device having corresponding connecting features such as external threads.

Returning to FIGS. 21A-21B, the operating tool 400 may include a housing 410 configured to receive or enclose the gear assembly 408, rotatably secure the driving shafts 404, 406 and optionally the outer connection shafts 414, 416. FIGS. 28A-28E illustrate an exemplary housing according to embodiments of the disclosure. As shown, the housing 410 may be ergonomically shaped for ease of holding by the user. The housing 410 can also be designed in any other suitable shapes or configurations. The housing 410 may include a first end portion 410a proximal to the handle 402 and a second end portion 410b distal to the handle 402. In the first end portion 410a, a cavity 430 may be provided for receiving the gear assembly 408. A teeth-like configuration 428 may be built in the internal surface of the housing for receiving or locking the second gear member 408b. Opening 432 may be provided in the side of the housing 410 for receiving a rubber slide 409 and allowing displacement of the lever member 408c. Channels 434a, 434b may be provided for receiving the first portions 404a, 406a of the first and second driving shafts 404, 406 respectively. Channels 436a, 436b may be provided in the second end portion 410b of the housing 410 for receiving the first end portions 414a, 416a of the first and second tubular shafts 414, 416. At the second end portion 410b of the housing 410, apertures or passages 438 may be provided for receiving screws 418, pins, keys or the like (FIG. 21B) to rotatably secure the driving shafts 404, 406 to the housing 410. Optionally, apertures or passages 440 may be provided for receiving screws 419, pins, keys or the like (FIG. 21B), to rotatably secure the outer connection shafts 414, 416 to the housing 410.

FIG. 29 shows with greater clarity the driving shafts 404, 406 and outer connection shafts 414, 416 rotatably secured to the second end 410b of the housing 410. As shown, when assembled screws 418, keys, pins or the like may flush against the rounded portion with a reduced diameter of the first and second driving shafts 404, 406, preventing the driving shafts 404, 406 from sliding out of the housing 410 in the axial direction while allowing the driving shafts 404, 406 to freely spin or rotate. Likewise, screws 419, keys, pins or the like may flush against the rounded portion with a reduced diameter of the first and second tubular shafts 414, 416, preventing the tubular shafts 414, 416 from sliding out of the housing 410 in the axial direction while allowing the tubular shafts 414, 416 to freely spin or rotate.

Returning to FIGS. 21A-21B, the operating tool 400 may include an adapter 420 configured to connect the first driving shaft 404 with the handle 402. FIG. 30 illustrates an exemplary adapter 420 according to embodiments of the disclosure. As shown, the adapter 420 may include a first end portion 420a and a second end portion 420b. The first end portion 420a of the adapter 420 may be shaped and sized to be received by the handle 402. The second end portion 420b may be provided with a channel 442 configured to receive the first driving shaft 404. As shown, the channel 442 may be shaped or configured to allow the end portion 404d (FIG. 22A) of the first driving shaft 404 to freely sliding into or out of the channel 442 during assembly or disassembly and prevent the driving shaft 404 from rotating relative to the adapter 420 once the end portion 404d is received in the channel 442. An aperture or passage 444 on the side of the second end portion 420b may be provided for receiving a screw, key, pin or the like to secure the first driving shaft 404 to the adapter 420. The use of an adapter allows the first and second driving shafts 404, 406 to be made in the same length and/or geometry. As such, the cost of the operating tool 400 can be significantly reduced since the first and second driving shafts 404, 406 may be manufactured in a same style and the number of parts needed in the manufacturing is reduced.

Returning to FIGS. 21A-21B, the operating tool 400 may include a first dial 446 for providing the user with information about revolution(s) of the first driving shaft 404. The first dial 446 may be operably coupled to and rotated with the first driving shaft 404 when in operation. FIG. 31 illustrates an exemplary dial which can be used as the first dial of the operating tool. As shown, the first dial 446 may include indicia 448 indicating revolution(s) of the dial and an aperture 450 configured to allow the first driving shaft 404 or the adapter 420 coupled to the first driving shaft 404 to fit in. In use, the first dial 446 rotates with the first driving shaft 404 and the indicia 448 on the first dial 446 provide the user with information about revolution(s) of first driving shaft 404.

Referring to FIGS. 21A-21B, the operating tool 400 may also include a second dial 452 for providing the user with information about revolution(s) of the second driving shaft 406. The second dial 452 may be operably coupled to and rotated with the second driving shaft 406 when in operation. FIG. 32 illustrates an exemplary dial 452 which can be used as the second dial of the operating tool. As shown, the second dial 452 may include indicia 454 indicating revolution(s) of the dial and a portion having a channel 456 configured to receive the second driving shaft 406. In use, the second dial 452 rotates with the second driving shaft 406 and the indicia 454 on the second dial 452 provide the user with information about revolution(s) of the second driving shaft 406. When the second driving shaft 406 is coupled with the first driving shaft 404 by the gear assembly 408 in operation wherein the handle 402 rotates both the first and second driving shafts 404, 406, both the first dial 446 and second dial 452 revolve, providing an indication to the user of a first operating mode of the operating tool. When the second driving shaft 406 is decoupled from the first driving shaft 404 by the gear assembly 408 wherein the handle 402 rotates solely the first driving shaft 404, only the first dial 446 coupled to the first driving shaft 404 revolves, providing an indication to the user of a second operating mode of the operating tool.

Referring to FIGS. 21A-21B, in use the operating tool 400 may be connected with a workpiece such as a spinal implant device (not shown) via outer connection or tubular shafts 414, 416. The user may spin or rotate the outer connection shafts 414, 416, for example, inwards to thread the operating tool 400 onto the implant device. In connecting with the implant device, the user may first place the lever member 408c in the locked position (e.g. the middle position in FIG. 26) so that the gear members 408a, 408b are locked in the housing 410 and rotations of the driving shafts 404, 406 by the handle 402 are prohibited.

Once the operating tool 400 is connected with the implant device, to achieve expansion of the implant device, the user may place the lever member 408c to the expansion position (e.g. the proximal position in FIG. 24) so that the first and second gear members 408a, 408b are free from the locked position and engaged to couple the first and second driving shafts 404, 406. The user may then rotate the handle 402 in a direction e.g. clockwise to apply torque to the first driving shaft 404. The rotation of the first driving shaft 404 simultaneously causes rotation of the second driving shaft 406, thereby effecting expansion of the implant device in fine increments. If desired the user may rotate the handle 402 in an opposite direction e.g. counterclockwise, to contract or finely adjust the expansion level of the implant device. In some embodiments, the gear members 408a, 408b may be configured such that a rotation of the first driving shaft 404 in a first direction, e.g. clockwise, causes a rotation of the second driving shaft 406 in a second direction opposite to the first direction, e.g. counterclockwise. Alternatively, the gear members 408a, 408b may be configured such that rotating the handle 402 causes the first and second driving shafts 404, 406 to rotate in the same direction.

To achieve lordosis, the user may place the lever 408c to the lordosis position (e.g. the distal position in FIG. 25) so that the first and second gear members 408a, 408b are disengaged thereby decoupling the second driving shaft 406 from the first driving shaft 404. The user may then rotate the handle 402 in a direction e.g. clockwise, applying torque solely to the first driving shaft 404 since the second driving shaft 406 becomes inactive. The rotation of only the first driving shaft 404 causes the implant device to tilt, thereby achieving lordosis. If desired, the user may rotate the handle 402 in an opposite direction, e.g. counterclockwise, to adjust or remove the levels of the lordosis.

To disconnect the operating tool 400 from the implant device, the user may place the lever member 408c to the locked position and then spin the outer connection or tubular shaft 414, 416 e.g. outwards to unthread the operating tool 400 from the implant device.

Embodiments of an operating instrument have been described. Those skilled in the art will appreciate that various other modifications may be made within the spirit and scope of the invention. For example, while embodiments of an exemplary operating instrument are described in connection with the drawings depicting straight driving shafts and straight outer connection shafts, in some embodiments, the drive shafts, and optionally the outer connection shafts, may include a portion that is angled with respect to a straight portion of the driving and outer connection shafts, e.g., ranging from 0 to 90 degrees. The angled driving shafts allow a surgeon to reach lumbar disc space segments in certain patients who are not accessible from straight on. The angled and straight portions may be machined as a single driving or outer connection shaft component, or alternatively, separately machined and then assembled as a driving or outer connection shaft. In some embodiments, the angled portion may be an adapter-type piece that can be inserted or connected onto an existing set of straight drive shafts or outer connection shafts. By way of example, the outer connection shafts can be angled through a variation of a ball joint which allows for perpendicular torqueing. The driving shafts can be angled through some variation of a ball joint, worm gear, or bevel gear configuration which allows for perpendicular torqueing.

All these or other variations and modifications are contemplated by the inventors and within the scope of the invention.

What is claimed is:

1. An operating instrument, comprising:
   a handle;
   a first driving shaft operably connected with the handle;
   a second driving shaft; and
   a gear assembly comprising a first gear member received on the first driving shaft, a second gear member slidably received on the second driving shaft, and a lever operable to place the second gear member into engagement with the first gear member by moving the second gear member along a longitudinal axis of the second driving shaft into a first position, thereby coupling the second driving shaft with the first driving shaft to provide a first operating mode wherein the handle operates to rotate both the first and second driving shafts, and place the second gear out of engagement with the first gear member by moving the second gear member along the longitudinal axis of the second driving shaft into a second position, thereby decoupling the second driving shaft from the first driving shaft to provide a second operating mode wherein the handle operates to rotate solely the first driving shaft, wherein the longitudinal axis of the second driving shaft extends along the longest length of the second driving shaft.

2. The operating instrument of claim 1, further comprising a housing provided with a cavity configured to receive the gear assembly and a first portion of the first and second driving shafts, wherein a second portion of the first and second driving shafts extends out of the housing.

3. The operating instrument of claim 2, wherein the first and second driving shafts are rotatably secured to the housing respectively thereby preventing the first and second driving shafts from axially moving out of the housing while allowing the first and second driving shafts to rotate.

4. The operating instrument of claim 2, further comprising:
   a first tubular shaft surrounding the second portion of the first driving shaft and a second tubular shaft surrounding the second portion of the second driving shaft,
   wherein the first and second tubular shafts each comprises a first end portion rotatably secured to the housing, thereby preventing the first and second tubular shafts from axially moving out of the housing while allowing the first and second tubular shafts to rotate independently of rotations of the first and second driving shafts respectively.

5. The operating instrument of claim 4, wherein the first and second tubular shafts each comprises a workpiece-connecting end provided with threads configured to connect with a workpiece having corresponding threads.

6. The operating instrument of claim 4, wherein at least one of the first and second tubular shafts comprises a finger grip.

7. The operating instrument of claim 2, wherein the lever is further operable to place the second gear member in a locked position in the housing by moving the second gear member along the longitudinal axis of the second driving shaft into a third position, wherein a rotation of the second and first driving shafts by the handle is prohibited.

8. The operating instrument of claim 7, wherein an internal surface of the housing is provided with a teeth-configuration configured to mate with at least a portion of the second gear member in the locked position.

9. The operating instrument of claim 2, further comprising a first dial operably coupled to the first driving shaft indicating revolution(s) of the first driving draft.

10. The operating instrument of claim 9, further comprising a second dial operably coupled to the second driving shaft indicating revolution(s) of the second driving draft.

11. The operating instrument of claim 1, further comprising an adapter connecting the first driving shaft with the handle.

12. The operating instrument of claim 11, wherein the first and second driving shafts have a substantially same length and cross-sectional geometry along the length.

13. The operating instrument of claim 1, wherein the first and second gear members are configured such that when the first and second gear members are operably engaged a rotation of the first driving shaft by the handle in a first direction causes a rotation of the second driving shaft in a second direction opposite to the first direction.

14. An operating instrument, comprising:
   a handle;
   a housing;
   a first driving shaft operably connected with the handle, the first driving shaft comprising a first portion received in the housing and a second portion extending out of the housing;
   a second driving shaft comprising a first portion received in the housing and a second portion extending out of the housing, wherein the first and second driving shafts are rotatably secured to the housing respectively thereby preventing the first and second driving shafts from axially moving out of the housing while allowing the first and second driving shafts to rotate;
   a first tubular shaft surrounding the second portion of the first driving shaft;
   a second tubular shaft surrounding the second portion of the second driving shaft, wherein the first and second tubular shafts are rotatably secured to the housing respectively, thereby preventing the first and second tubular shafts from axially moving out of the housing while allowing the first and second tubular shafts to rotate independently of rotations of the first and second driving shafts respectively, and
   a gear assembly received in the housing operable to couple the second driving shaft with the first driving shaft to provide a first operating mode wherein the handle operates to rotate both the first and second driving shafts, or decouple the second driving shaft from the first driving shaft to provide a second operating mode wherein the handle operates to rotate solely the first driving shaft, the gear assembly comprising a first gear member received on the first driving shaft, a second gear member slidably received on the second driving shaft, and a lever operable to place the second gear member into engagement with the first gear member and place the second gear out of engagement with the first gear member by moving the second gear member along a longitudinal axis of the second driving shaft, wherein the longitudinal axis of the second driving shaft extends along the longest length of the second driving shaft.

15. The operating instrument of claim 14, further comprising an adapter connecting the first driving shaft with the handle.

16. The operating instrument of claim 15, wherein the first and second driving shafts have a substantially same length and cross-sectional geometry along the length.

17. The operating instrument of claim 14, further comprising a first dial operably coupled to the first driving shaft indicating revolution(s) of the first driving draft.

18. The operating instrument of claim 17, further comprising a second dial operably coupled to the second driving shaft indicating revolution(s) of the second driving draft.

19. The operating instrument of claim 14, wherein the gear assembly is further operable to lock the second and first driving shafts thereby prohibiting the second and first driving shafts from rotating.

20. The operating instrument of claim 19, wherein an internal surface of the housing is provided with a teeth-configuration configured to mate with a portion of the gear assembly in locking the second and first driving shafts.

21. The operating instrument of claim 20, wherein the gear assembly is configured such that in the first operating mode a rotation of the first driving shaft by the handle in a first direction causes a rotation of the second driving shaft in a second direction opposite to the first direction.

* * * * *